[12] United States Patent
Kalafut et al.

(10) Patent No.: US 9,238,099 B2
(45) Date of Patent: Jan. 19, 2016

(54) SYSTEM AND APPARATUS FOR MODELING PRESSURES GENERATED DURING AN INJECTION PROCEDURE

(75) Inventors: John F. Kalafut, Pittsburgh, PA (US); David A. Mishler, Slippery Rock, PA (US)

(73) Assignee: Bayer HealthCare LLC, Whippany, NJ (US)

(*) Notice: Subject to any disclaimer, the term of this patent is extended or adjusted under 35 U.S.C. 154(b) by 280 days.

(21) Appl. No.: 11/691,823

(22) Filed: Mar. 27, 2007

(65) Prior Publication Data
US 2007/0213662 A1 Sep. 13, 2007

Related U.S. Application Data

(63) Continuation of application No. 11/576,060, filed as application No. PCT/US2005/042891 on Nov. 23, 2005.

(60) Provisional application No. 60/631,015, filed on Nov. 24, 2004.

(51) Int. Cl.
 *A61M 5/00* (2006.01)
 *A61M 5/145* (2006.01)
 (Continued)

(52) U.S. Cl.
 CPC ............ *A61M 5/007* (2013.01); *A61M 5/14546* (2013.01); *G06F 19/3406* (2013.01); *A61B 6/507* (2013.01); *A61M 5/16854* (2013.01);
 (Continued)

(58) Field of Classification Search
 CPC ............... A61M 5/14546; A61M 5/16854; A61M 5/16859; A61M 2005/14208; A61M 2205/3334; A61M 2205/50; A61M 2230/04; A61B 6/507

USPC ............................................ 604/67, 118, 505
See application file for complete search history.

(56) References Cited

U.S. PATENT DOCUMENTS 3,349,713 A 10/1967 Fassbender
3,520,295 A 7/1970 Kelly
(Continued)

FOREIGN PATENT DOCUMENTS

AT 259621 T 3/2004
AU 7381796 A 4/1997
(Continued)

OTHER PUBLICATIONS

"The Solution for Your IV Formulas", Valley Lab. Inc., E-39-15, 3399, 3400, 2646.
(Continued)

*Primary Examiner* — Kami A Bosworth
*Assistant Examiner* — Brandy S Lee
(74) *Attorney, Agent, or Firm* — James R. Stevenson; Henry E. Bartony, Jr.; Gregory L. Bradley

(57) ABSTRACT

A fluid injection apparatus includes at least one pressurizing mechanism and at least a first fluid container (for example, a syringe or a bulk container) operably associated with the at least one pressurizing mechanism. The first fluid container is adapted to contain a first fluid to be injected. The fluid injection apparatus also includes a pressure modeling system adapted to predict a pressure to be generated at one or more points in the injection fluid path during planned injection procedure based upon variables associated with an injection protocol.

21 Claims, 24 Drawing Sheets

(51) Int. Cl.
  *G06F 19/00* (2011.01)
  *A61M 5/168* (2006.01)
  *A61M 5/142* (2006.01)
  *A61B 6/00* (2006.01)

(52) U.S. Cl.
  CPC ........... *A61M2005/14208* (2013.01); *A61M 2205/3334* (2013.01); *A61M 2205/50* (2013.01); *A61M 2230/04* (2013.01)

(56) References Cited

U.S. PATENT DOCUMENTS

| | | |
|---|---|---|
| 3,523,523 A | 8/1970 | Reich |
| 3,623,474 A | 11/1971 | Heilman et al. |
| 3,701,345 A | 10/1972 | Heilman et al. |
| 3,755,655 A | 8/1973 | Sewecal |
| 3,793,600 A | 2/1974 | Groubard |
| 3,812,843 A | 5/1974 | Wjutten et al. |
| 3,817,843 A | 6/1974 | Barrett |
| 3,839,708 A | 10/1974 | Bredesen et al. |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,006,736 A | 2/1977 | Kranys et al. |
| 4,001,549 A | 8/1977 | LeFebre et al. |
| 4,038,981 A | 8/1977 | LeFevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,207,871 A | 6/1980 | Jenkins |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrover, Jr. et al. |
| 4,284,073 A | 8/1981 | Krause |
| 4,315,247 A | 2/1982 | Germanton |
| 4,319,568 A | 3/1982 | Tregouing |
| 4,340,153 A | 7/1982 | Spivey |
| 4,341,153 A | 7/1982 | Browser |
| 4,392,847 A | 7/1983 | Whitney et al. |
| 4,392,849 A | 7/1983 | Petre et al. |
| 5,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers De Beyl et al. |
| 4,552,130 A | 11/1985 | Kinoshita |
| 4,559,036 A | 12/1985 | Wunsch |
| 4,563,175 A | 1/1986 | LaFond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubata |
| 4,689,670 A | 8/1987 | Okazaki |
| 4,710,166 A | 12/1987 | Thompson et al. |
| 4,723,261 A | 2/1988 | Jannsen et al. |
| 4,750,643 A | 6/1988 | Wertrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | DiGianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A * | 8/1989 | Hirschman et al. ........... 600/432 |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | DiGianfilippo et al. |
| 5,059,173 A | 10/1991 | Sacco |
| 5,061,243 A | 10/1991 | Winchell et al. |
| 5,069,662 A | 12/1991 | Bodden |

(56) References Cited

U.S. PATENT DOCUMENTS

| | | | |
|---|---|---|---|
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Asianian |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Eilman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata |
| 5,276,614 A | 1/1994 | Heuscher |
| 5,286,252 A | 2/1994 | Tuttle et al. |
| 5,287,273 A | 2/1994 | Kupfer et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Mormoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hauge et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kampfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | DeVale |
| 5,468,240 A | 11/1995 | Genetelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,881,124 A | 3/1999 | Giger et al. |
| 5,882,343 A | 3/1999 | Wilson et al. |
| 5,885,216 A | 3/1999 | Evans |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae |
| 6,056,902 A * | 5/2000 | Hettinga ............... 264/40.1 |
| 6,063,052 A | 5/2000 | Uber, III et al. |
| 6,073,042 A | 6/2000 | Simonetti |
| 6,099,502 A | 8/2000 | Duchon et al. |
| 6,149,627 A | 11/2000 | Uber |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,344,030 B1 | 2/2002 | Duchon et al. |
| 6,381,486 B1 | 4/2002 | Mistretta et al. |

(56) References Cited

U.S. PATENT DOCUMENTS

| | | |
|---|---|---|
| 6,385,483 B1 | 5/2002 | Uber, III et al. |
| 6,387,098 B1 | 5/2002 | Cole et al. |
| 6,397,093 B1 | 5/2002 | Aldrich |
| 6,397,097 B1 | 5/2002 | Requardt |
| 6,397,098 B1 | 5/2002 | Uber, III et al. |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell Gisper Sauch et al. |
| 6,520,930 B2 * | 2/2003 | Critchlow et al. ............. 604/67 |
| 6,527,718 B1 | 3/2003 | Connor et al. |
| 6,554,819 B2 | 4/2003 | Reich |
| 6,556,695 B1 | 4/2003 | Packet et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Wilson et al. |
| 6,673,033 B1 | 1/2004 | Sciulli et al. |
| 6,685,733 B1 | 2/2004 | Dae et al. |
| 6,691,047 B1 * | 2/2004 | Fredericks ...................... 702/47 |
| 6,699,219 B2 | 3/2004 | Emig et al. |
| 6,731,971 B2 | 5/2004 | Evans, III et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,901,283 B2 | 5/2005 | Evans, III et al. |
| 6,970,735 B2 | 11/2005 | Uber, III et al. |
| 6,983,590 B2 * | 1/2006 | Roelle et al. ................... 60/289 |
| 7,094,216 B2 | 8/2006 | Trombley, III et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,313,431 B2 | 12/2007 | Uber, III et al. |
| 7,925,330 B2 | 4/2011 | Kalafut et al. |
| 8,295,914 B2 | 10/2012 | Kalafut et al. |
| 8,486,017 B2 | 7/2013 | Masuda et al. |
| 2001/0027265 A1 | 10/2001 | Prince |
| 2001/0056233 A1 | 12/2001 | Uber, III et al. |
| 2002/0010551 A1 | 1/2002 | Wang et al. |
| 2002/0026148 A1 | 2/2002 | Uber, III et al. |
| 2002/0091349 A1 | 7/2002 | Reich |
| 2002/0099254 A1 | 7/2002 | Movahed |
| 2002/0123702 A1 | 9/2002 | Cho |
| 2002/0151854 A1 | 10/2002 | Duchon et al. |
| 2002/0165445 A1 | 11/2002 | Uber et al. |
| 2003/0036694 A1 | 2/2003 | Liu |
| 2003/0050556 A1 | 3/2003 | Uber, III et al. |
| 2003/0120171 A1 | 6/2003 | Diamantopoulos et al. |
| 2003/0135111 A1 | 7/2003 | Meaney et al. |
| 2003/0195462 A1 | 10/2003 | Mann et al. |
| 2003/0212364 A1 | 11/2003 | Mann et al. |
| 2003/0216683 A1 * | 11/2003 | Shekalim .................... 604/67 |
| 2004/0008028 A1 | 1/2004 | Horger et al. |
| 2004/0010229 A1 | 1/2004 | Houde et al. |
| 2004/0011740 A1 | 1/2004 | Bernard et al. |
| 2004/0015078 A1 | 1/2004 | Evans et al. |
| 2004/0025452 A1 | 2/2004 | McLean |
| 2004/0044302 A1 | 3/2004 | Bernard et al. |
| 2004/0064040 A1 | 4/2004 | Masuda et al. |
| 2004/0064041 A1 | 4/2004 | Lazzaro et al. |
| 2004/0074453 A1 | 4/2004 | Roelle et al. |
| 2004/0097806 A1 | 5/2004 | Hunter et al. |
| 2004/0097875 A1 | 5/2004 | Bae |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2006/0079843 A1 * | 4/2006 | Brooks et al. ................. 604/151 |

FOREIGN PATENT DOCUMENTS

| | | |
|---|---|---|
| CA | 2077712 A1 | 12/1991 |
| CA | 2045070 | 2/1992 |
| CA | 2234050 A1 | 4/1997 |
| DE | 3203594 A1 | 8/1983 |
| DE | 3726452 | 2/1989 |
| DE | 4121568 A1 | 10/1992 |
| DE | 4426387 | 8/1995 |
| DE | 19702896 A1 | 7/1997 |
| DE | 19647701 A1 | 5/1998 |
| DE | 69530035 T2 | 9/2003 |
| DK | 0869738 T3 | 6/2004 |
| EP | 0121216 A1 | 10/1984 |
| EP | 0129910 A1 | 1/1985 |
| EP | 0189491 | 8/1986 |
| EP | 0192786 A2 | 9/1986 |
| EP | 0245160 A1 | 11/1987 |
| EP | 0319275 | 11/1988 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 | 10/1994 |
| EP | 0439711 | 5/1995 |
| EP | 0650738 A1 | 5/1995 |
| EP | 0650739 A1 | 5/1995 |
| EP | 0702966 A2 | 3/1996 |
| EP | 0869738 A1 | 10/1998 |
| EP | 1262206 A2 | 12/2002 |
| ES | 2216068 T3 | 10/2004 |
| FR | 2493708 | 5/1982 |
| FR | 2561949 | 10/1985 |
| GB | 201800 A | 8/1923 |
| GB | 2252656 A | 8/1992 |
| GB | 2328745 A | 3/1999 |
| JP | 50-017781 | 2/1975 |
| JP | 58-015842 | 1/1983 |
| JP | 59-214432 | 12/1984 |
| JP | 60-194934 | 10/1985 |
| JP | 60-194935 | 10/1985 |
| JP | 60-253197 | 12/1985 |
| JP | 62-216199 | 9/1987 |
| JP | 63040538 A | 2/1988 |
| JP | 63-290547 | 11/1988 |
| JP | 01-207038 | 8/1989 |
| JP | 02-224647 | 9/1990 |
| JP | 02-234747 | 9/1990 |
| JP | 03-055040 | 3/1991 |
| JP | 04-115677 | 4/1992 |
| JP | 05-084296 | 4/1993 |
| JP | 07-178169 | 7/1995 |
| JP | 10-211198 | 8/1998 |
| JP | 2000506398 A | 5/2000 |
| JP | 2000175900 A | 6/2000 |
| JP | 2003-225234 | 1/2002 |
| JP | 2003-102724 A | 4/2003 |
| JP | 2003-116843 | 4/2003 |
| JP | 2003-210456 | 7/2003 |
| JP | 2004174008 A | 6/2004 |
| JP | 3553968 B2 | 8/2004 |
| JP | 2004236849 A | 8/2004 |
| JP | 2004298550 A | 10/2004 |
| WO | 8001754 A1 | 9/1980 |
| WO | 85/00292 | 1/1985 |
| WO | 88/03815 | 6/1988 |
| WO | 9114232 A1 | 9/1991 |

(56) References Cited

FOREIGN PATENT DOCUMENTS

| WO | 9114233 A1 | 9/1991 |
| --- | --- | --- |
| WO | 9315658 A1 | 8/1993 |
| WO | 9325141 A1 | 12/1993 |
| WO | 94/15664 | 7/1994 |
| WO | 9632975 A1 | 10/1996 |
| WO | 9712550 A1 | 4/1997 |
| WO | 98/20919 | 5/1998 |
| WO | 9924095 A2 | 5/1999 |
| WO | 0061216 A1 | 10/2000 |
| WO | 0064353 A2 | 11/2000 |
| WO | 03015633 A1 | 2/2003 |
| WO | 2004012787 A2 | 2/2004 |
| WO | 2005016165 A1 | 2/2005 |
| WO | 2006042093 A1 | 4/2006 |

OTHER PUBLICATIONS

InfusO.R. Multi-Drug Syringe Pump with Smart Labels:, Bard MedSystems Division Inc., 2693-2696.
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
Non-Final Office Action mailed Nov. 5, 2012, in U.S. Appl. No. 13/186,983, John F. Kalafut et al., filed Jul. 20, 2011.
Non-Final Office Action mailed Oct. 18, 2012, in U.S. Appl. No. 12/519,213, John F. Kalafut et al., filed Jun. 15, 2009.
Supplementary European Search Report mailed Jul. 23, 2013 in European Patent Application No. 08771789.8.
Supplementary European Search Report mailed Dec. 9, 1998 in European Patent Application No. EP 96936079.0.
Non-Final Office Action mailed Sep. 17, 2012, in U.S. Appl. No. 12/611,172, John F. Kalafut et al., filed Nov. 3, 2009.
Østergaard, L., et al., "High resolution measurement of cerebral blood flow using intravascular tracer bolus passages. Part 1: Mathematical approach and statistical analysis," Magnetic Resonance in Medicine, vol. 36, Issue 5, pp. 715-725, 1996.
Østergaard, L., et al., "High resolution measurement of cerebral blood flow using intravascular tracer bolus passages. Part II: Experimental comparison and preliminary results," Magn Reson Med, vol. 36, Issue 5, pp. 726-736, 1996.
Supplementary European Search Report mailed Aug. 19, 2010 in European Patent Application No. 05852259.0.
Supplementary European Search Report mailed Apr. 15, 2011 in European Patent Application No. 07867951.1.
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
Rosen, B.R. et al., "Perfusion Imaging with NMR Contrast Agents," Magentic Resonance in Medicine, vol. 14, No. 2, pp. 249-265, May 1, 1990.
Parker, K.J. and Tuthill T.A., "A Particulate Contrast Agent With Potential for Ultrasound Imaging of Liver," Ultrasound in Medicine & Biology vol. 13, Issue 9, pp. 555-566, Sep. 1987.
European Search Report mailed Feb. 21, 2012 in European Patent Application No. 11001045.1.
Harris P., H. D. "The Human Pulmonary Circulation," Edinburgh, Churchill Livingstone, (Appendix I), 1986.
Hayes, M.H., "Statistical Digital Signal Processing and Modeling," New York, New York: Wiley and Sons, pp. 154-177, 1996.
Heiken, J.P. et al., "Dynamic Contrast-Enhanced CT of the Liver: Comparison of Contrast Medium Injection Rates and Uniphasic and Biphasic Injection Protocols," Radiology, vol. 187, No. 2, May 1993, pp. 327-331.
International Preliminary Report on Patentability, International Search Report and Written Opinion for International Patent Application No. PCT/US00/10842 issued May 22, 2001.
International Preliminary Report on Patentability, International Search Report, and Written Opinion for International Patent Application No. PCT/US2007/026194 issued Jun. 30, 2009.
International Preliminary Report on Patentability, International Search Report , and Written Opinion for International Patent Application No. PCT/US2007/087765 issued Jun. 30, 2009.
International Preliminary Report on Patentability, International Search Report , and Written Opinion for International Patent Application No. PCT/US2008/067982 issued Jan. 19, 2010.
International Preliminary Report on Patentability, International Search Report , and Written Opinion for International Patent Application No. PCT/US2009/047168 issued Jan. 5, 2011.
International Preliminary Report on Patentability, International Search Report , and Written Opinion for International Patent Application No. PCT/US2011/041802 issued Dec. 28, 2012.
International Preliminary Report on Patentability and Wrtitten Opinion for International Patent Application No. PCT/US2005/042891 issued May 30, 2007.
International Preliminary Report on Patentability for International Application No. PCT/EP2005/007791, International Bureau of WIPO, Geneva, Switzerland, issued on May 22, 2007.
International Preliminary Report on Patentability for International Patent Application No. PCT/US2005/041913 issued May 22, 2007.
International Search Report and Written Opinion for International Application No. PCT/US05/42891, ISA/US mailed on Sep. 25, 2006.
European Search Report mailed Jan. 30, 2003 in European Patent Application No. 02020247.9.
European Search Report mailed Jun. 17, 1996 in European Patent Application No. 95202547.6.
EZ Chem Brochure, E-Z-EM, Inc., Jul. 2007.
Final Office Actions mailed Jun. 17, 2013 and Mar. 4, 2013, in U.S. Appl. No. 12/519,213, John F. Kalafut et al., filed Jun. 15, 2009.
International Search Report for International Patent Application No. PCT/US96/15680 mailed Jan. 28, 1997.
Ireland, M.A., et al., "Safety and Convenience of a Mechanical Injector Pump for Coronary Angiography," Catheterization and Cardiovascular Diagnosis, vol. 16, Issue 3, pp. 199-201, 1989.
Final Office Action mailed Jun. 19, 2013, in U.S. Appl. No. 13/186,983, John F. Kalafut et al., filed Jul. 20, 2011.
Final Office Action mailed May 10, 2013, in U.S. Appl. No. 12/611,172, John F. Kalafut et al., filed Nov. 3, 2009.
Final Office Action mailed Oct. 2, 2012, in U.S. Appl. No. 12/519,040, John F. Kalafut, filed Jun. 12, 2009.
Flegal, K.M., et al., "Prevalence and trends in obesity among US adults," JAMA, 2002, vol. 288, Issue 14, pp. 1-4, 1999-2000.
Fleischmann, D., "Contrast Medium Injection Technique," In: U. Joseph Schoepf: "Multidetector—Row CT of The Thorax," pp. 47-59, Jan. 22, 2004.
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Krause, W., "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., C02-Power-Assisted Hand-Held Syringe: Better Visualization during Diagnostic and Interventional, vol. 19, Issue 2, pp. 123-128, Feb. 1990.
Mark V/Mark V Plus Injector Operation Manual KMP 805P Rev. B. Medrad, Inc, 1990.
McClellan, J.H., "Parametric Signal Modeling," Chapter 1 in Advanced Topics in Signal Processing, Pentice-Hall, Englewood Cliffs, NJ, 1988.
Gardiner, G. A., et al., "Selective Coronary Angiography Using a Power Injector," AJR Am J Roentgenol., vol. 146, Issue 4, pp. 831-833, Apr. 1986.
MCT and MCT Plus Injection Systems Operation Manual KMP 810P, MEDRAD, Inc. 1991.
Gembicki, F.W., "Vector Optimization for Control with Performance and Parameter Sensitivity Indices," PhD Thesis, Case Western Reserve University, 1974.
Gerlowski L.E. and Jain R.K., "Physiologically Based Pharmacokinetic Modeling: Principles and Applications," Journal of Pharmaceutical Sciences, vol. 72, pp. 1104-1125, Oct. 1983.

(56) References Cited

OTHER PUBLICATIONS

Goss, J. E., et al., "Power injection of contrast media during percutaneous transluminal coronary artery angioplasty," Catheterization and Cardiovascular Diagnosis, vol. 16, pp. 195-198 1989.
Non-Final Office Actions mailed Apr. 26, 2013 and on Feb. 15, 2012, in U.S. Appl. No. 12/519,040, John F. Kalafut, filed Jun. 12, 2009.
Grant, S.C.D. et al., "Reduction of Radiation Exposure to the Cardiologist during Coronary Angiography by the Use of A Remotely Controlled Mechanical Pump for Injection of Contrast Medium," Catheterization and Cardiovascular Diagnosis, vol. 25, Issue 2, pp. 107-109, Feb. 1992.
Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.
Hansen, P.C, Regularization tools: a MATLAB package for analysis and solution of discrete ill-posed problems, Numerical Algorithms, vol. 6, Issue 1, pp. 35, 1994.
Hansen, P.C., "The truncated SVD as a method for regularization," BIT Numerical Mathematics, vol. 27, Issue 4, pp. 534-555, 1987.
Non-Final office Action mailed Mar. 12, 2013, in U.S. Appl. No. 13/655,525, John F. Kalafut et al., filed Oct. 19, 2012.
Office Action mailed Jan. 3, 2014 in U.S. Appl. No. 11/691,823.
Search Report and Supplementary European Search Report for EP05849688 dated Mar. 21, 2014.
European Search Report and Opinion mailed on Nov. 21, 2013 from EP No. 13004902.6.
Non-Final Office Action mailed Dec. 12, 2014, in U.S. Appl. No. 13/186,983.
Non-Final Office Action mailed Apr. 23, 2014, in U.S. Appl. No. 12/519,040, John F. Kalafut et al., filed Dec. 29, 2006.
Non-Final Office Action mailed Jul. 14, 2014 in related U.S. Appl. No. 12/519,213.
Sablayrolles, J-L, "Cardiac CT: Experience from Daily Practice", Advance CT, A GE Healthcare Publication. Aug. 2004.
Fleischmann, Dominik, "Present and Future Trends in Multiple Detector-Row CT Applications; CT Angiography", Eur. Radiol. 12 (Suppl. 2) 2002.
Korosec, Frank, "Basic Principles of Phase-contrast, Time-of-flight, and Contrast-enhanced MR Angiography", 1999.
Baker, Aaron; et al. "Fluid Mechanics Analysis of a Spring-Loaded Jet Injector." IEEE Transactions on Biomedical Engineering, vol. 46, No. 2, Feb. 1999.
Cademartiri, F. and Luccichenti, G., et al. (2004) "Sixteen-Row Multislice Computed Tomography:Basic Concepts, Protocols, and Enhanced Clinical Application," Semin Ultrasound CT MR 25(1):2-16.
K.T. Bae, J.P. Heiken, and J.A. Brink, "Aortic and Hepatic Contrast Medium Enhancement at CT. Part I. Prediction and a Computer Model," Radiology, vol. 207, pp. 647-655, 1998.
K.T. Bae, "Peak Contrast Enhancement in CT and MR Angiography: When Does It Occur and Why? Pharmacokinetic Study in a Porcine Model," Radiology, vol. 227, pp. 809-816, 2003.
K.T. Bae et al., "Multiphasic Injection Method for Uniform Prolonged Vascular Enhancement at CT Angiography: Pharmacokinetic Analysis and Experimental Porcine Method," Radiology, vol. 216, pp. 872-880, 2000.
D. Fleischmann and K. Hittmair, "Mathematical Analysis of Arterial Enhancement and Optimization of Bolus Geometry for CT Angiography Using the Discrete Fourier Transform," J Comput Assist Tomogr, vol. 23, pp. 474-484, 1999.
Fisher and Teo, "Optimal Insulin Infusion Resulting from a Mathematical Model of Blood Glucose Dyanamics", IEEE Trans Biomed Eng, vol. 36(4), pp. 479-486, 1989.
Jacobs, "Algorithm for Optimal Linear Model-Based Control with Application to Pharmacokinetic Model-Driven Drug Delivery", IEEE Trans Biomed Eng, vol. 37(1), pp. 107-109, 1990.
Wada and Ward, "The Hybrid Model: A New Pharmacokinetic Model for Computer-Controlled Infusion Pumps", IEEE Trans. Biomed. Eng, vol. 41(2), pp. 134-142, 1994.
Wada and Ward, "Open Loop Control of Multiple Drug Effects in Anesthesia", IEEE Trans. Biomed Eng, vol. 42(7), pp. 666-677, 1995.
Neatpisarnvanit and Boston, "Estimation of Plasma Insulin from Plasma Glucose", IEEE Trans Biomed Eng, vol. 49 (11), pp. 1253-1259, 2002.
Gentilini et al., "A New Paradigm for the Closed-Loop Intraoperative Administration of Analgesics in Humans", IEEE Tran Biomed Eng, vol. 49(4), pp. 289-2999, 2002.
Mahnken, A.H., Henzler, D, et al., "Determination of Cardiac Output with Multislice Spiral Computed Tomography: A Validation Study", Invest Radiol 39(8): 451-4, 2004.
Mahnken, A.H., Klotz, E., et al., "Measurement of Cardiac Output from a Test-Bolus Injection in Multislice Computed Tomography", Eur Radiol 13(11): 2498-504, 2003.
Garrett, J.S., Lanzer, P., et al., "Measurement of Cardiac Output by Cine Computed Tomography", Am J Cardiol 56 (10): 657-61, 1985.
The European Search Report from EP14174725.3 dated May 8, 2015.
"Angiomat 6000 Digital Injection System—Operator's Manual", Document No. 600950, Rev. 1—1990.
"Digital Injector for Angiography", Sias. (Sep. 7, 1993).
"Disposable Low-Cost Catheter Tip Sensor Measures Blood Pressure during Surgery," Sensor, Jul. 1989.
Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.
Angiography, Catheterization and Cardiovascular Diagnosis, vol. 19, pp. 123-128, 1990.
Awai, K., et al., "Aortic and hepatic enhancement and tumor-to-liver contrast: analysis of the effect of different concentrations of contrast material at multi-detector row helical CT.," Radiology, vol. 224, Issue 3, pp. 757-763, 2002.
Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.
Bae, K.T., et al., "Uniform vascular contrast enhancement and reduced contrast medium volume achieved by using exponentially decelerated contrast material injection method," Radiology, vol. 231, Issue 3, pp. 732-736, 2004.
Becker, C.R., et al., "Optimal contrast application for cardiac 4-detector-row computed tomography," Investigative Radiology, vol. 38, Issue 11, pp. 690-694, Nov. 2003.
Blomley, M.J.K. and Dawson, P., "Bolus Dynamics: Theoretical and Experimental Aspects," The Brit. J. of Radiology, 70, pp. 351-359, 1997.
Dardik, H. et al., "Remote Hydraulic Syringe Actuator," Arch. Surg., vol. 115, Issue 1, Jan. 1980.
Dawson, P. and M. Blomley, "The value of mathematical modelling in understanding contrast enhancement in CT with particular reference to the detection of hypovascular liver metastases," European Journal of Radiology, vol. 41, Issue 3, pp. 222-236, Mar. 2002.

\* cited by examiner

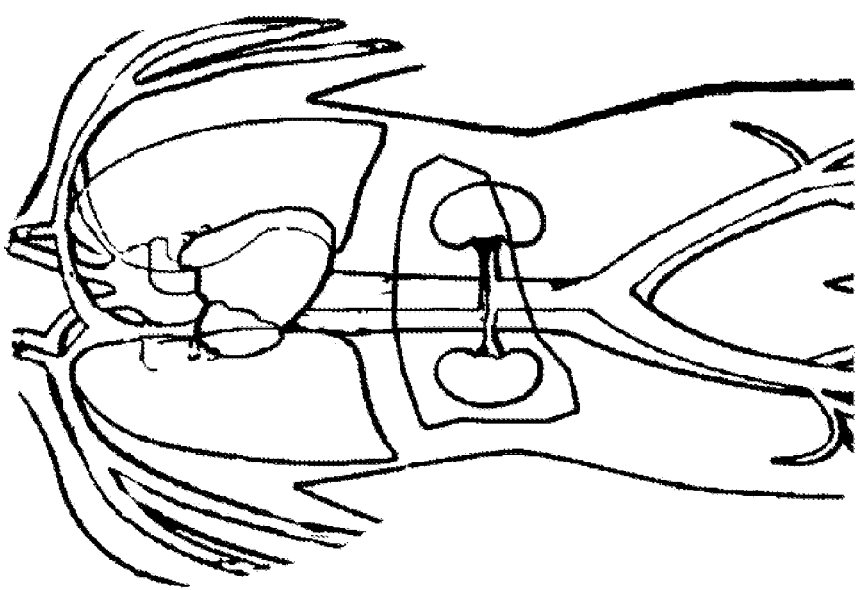
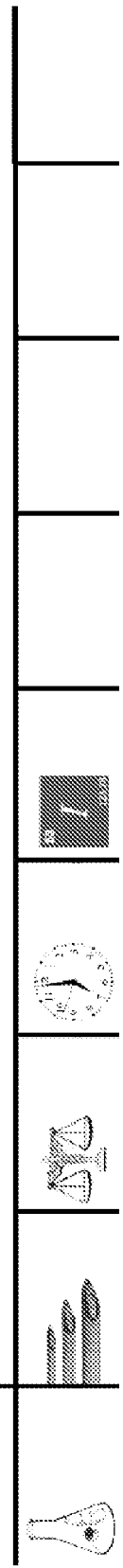
Fig. 2 if peak_enhancement$_{test}$ > 160 HU
ratio = 30/70
else if 120 < peak_enhancement$_{test}$ <= 160
ratio = 50/50
else if peak_enhancement$_{test}$ < 120
ratio = 70/30

|   | Flow Rate [ml/s] | Volume [ml] | Duration [sec] |
|---|---|---|---|
| A | 2.5 | 14 | 6 |
| B | 2.5 | 20 | 20 |

Estimated time to peak contrast enhancement 16 sec. [post injection start]

8 sec. [post injection start]

Close

Fig. 25B

SYSTEM AND APPARATUS FOR MODELING PRESSURES GENERATED DURING AN INJECTION PROCEDURE

CROSS-REFERENCE TO RELATED APPLICATION

This application is a continuation of application Ser. No. 11/576,060, filed on Mar. 27, 2007, which is a §371 national phase application of PCT International Application No. PCT/US2005/042891, filed on Nov. 23, 2005, and designating the United States of America, which claims benefit of U.S. Provisional Patent Application Ser. No. 60/631,015, filed Nov. 24, 2005, the disclosures of which are incorporated herein by reference.

BACKGROUND OF THE INVENTION

The present invention is relates to devices, systems and methods for fluid delivery, and, particularly, to devices, systems and methods for delivery of a pharmaceutical fluid to a patient, and, especially for delivery of a contrast medium to a patient during a medical injection procedure.

In many procedures, the administration of contrast medium (with an electronic power injector) for radiological exams starts with the clinician filling an empty, disposable syringe with a certain volume of contrast agent pharmaceutical. In other procedures, a syringe pre-filled with contrast agent is used. The clinician then determines a volumetric flow-rate and a volume of contrast to be administered to the patient to enable a diagnostic image. An injection of saline solution, having a volume and flow rate determined by the operator, often follows the administration of contrast agent into the veins or arteries. A number of currently available injectors allow for the operator to program a plurality of discrete phases of volumetric flow rates and volumes to deliver. For example, the SPECTRIS SOLARIS and STELLANT injectors available from Medrad, Inc. of Indianola, Pa., provide for entry of up to and including six discrete pairs or phases of volumetric flow rate and volume for delivery to a patient (for example, for contrast and/or saline). Such injectors and injector control protocols for use therewith are disclosed, for example, in U.S. Pat. No. 6,643,537 and Published U.S. Patent Application Publication No. 2004-0064041, assigned to the assignee of the present invention, the disclosures of which are incorporated herein by reference. The values or parameters within the fields for such phases are generally entered manually by the operator for each type of procedure and for each patient undergoing an injection/imaging procedure. Alternatively, earlier manually entered values of volume and flow rate can be stored and later recalled from the computer memory. However, the manner in which such parameters are to be determined for a specific procedure for a specific patient are not well developed.

In that regard, differences in contrast dosing requirements for different patients during imaging and other procedures have been recognized. For example, U.S. Pat. No. 5,840,026, assigned to the assignee of the present invention, the disclosure of which is incorporated herein by reference, discloses devices and methods to customize the injection to the patient using patient specific data derived before or during an injection. Although differences in dosing requirements for medical imaging procedures based upon patient differences have been recognized, conventional medical imaging procedures continue to use pre-set doses or standard delivery protocols for injecting contrast media during medical imaging procedures. Given the increased scan speed of recently available CT scanners including MDCT scanners, single phase injections are dominant over biphasic or other multiphasic injections in regions of the world where such fast scanners are used. Although using standard, fixed or predetermined protocols (whether uniphasic, biphasic or multiphasic) for delivery simplifies the procedure, providing the same amount of contrast media to different patients under the same protocol can produce very different results in image contrast and quality. Furthermore, with the introduction of the newest MDCT scanners, an open question in clinical practice and in the CT literature is whether the standard contrast protocols used with single-slice, helical scanners will translate well to procedures using the MDCT machines. See, for example, Cademartiri, F. and Luccichenti, G., et al., (2004). "Sixteen-row multislice computed tomography: basic concepts, protocols, and enhanced clinical applications." Semin Ultrasound CT MR 25(1): 2-16.

A few studies have attempted quantitative analyses of the injection process during CT angiography (CTA) to improve and predict arterial enhancement. For example, Bae and coworkers developed pharmacokinetic (PK) models of the contrast behavior and solved the coupled differential equation system with the aim of finding a driving function that causes the most uniform arterial enhancement. K. T. Bae, J. P. Heiken, and J. A. Brink, "Aortic and hepatic contrast medium enhancement at CT. Part I. Prediction with a computer model," Radiology, vol. 207, pp. 647-55, 1998; K. T. Bae, "Peak contrast enhancement in CT and MR angiography: when does it occur and why? Pharmacokinetic study in a porcine model," Radiology, vol. 227, pp. 809-16, 2003, K. T. Bae et al., "Multiphasic Injection Method for Uniform Prolonged Vascular Enhancement at CT Angiography: Pharmacokinetic Analysis and Experimental Porcine Method," Radiology, vol. 216, pp. 872-880, 2000, U.S. Pat. Nos. 5,583,902, 5,687,208, 6,055,985, 6,470,889 and 6,635,030, the disclosures of which are incorporated herein by reference. An inverse solution to a set of differential equations of a simplified compartmental model set forth by Bae et al. indicates that an exponentially decreasing flow rate of contrast medium may result in optimal/constant enhancement in a CT imaging procedure. However, the injection profiles computed by inverse solution of the PK model are profiles not readily realizable by most CT power injectors without major modification.

In another approach, Fleischmann and coworkers treated the cardiovascular physiology and contrast kinetics as a "black box" and determined its impulse response by forcing the system with a short bolus of contrast (approximating an unit impulse). In that method, one performs a Fourier transform on the impulse response and manipulates this transfer function estimate to determine an estimate of a more optimal injection trajectory than practiced previously. D. Fleischmann and K. Hittmair, "Mathematical analysis of arterial enhancement and optimization of bolus geometry for CT angiography using the discrete Fourier transform," J Comput Assist Tomogr, vol. 23, pp. 474-84, 1999, the disclosure of which is incorporated herein by reference.

Uniphasic administration of contrast agent (typically, 100 to 150 mL of contrast at one flow rate) results in a non-uniform enhancement curve. See, for example, D. Fleischmann and K. Hittmair, supra; and K. T. Bae, "Peak contrast enhancement in CT and MR angiography: when does it occur and why? Pharmacokinetic study in a porcine model," Radiology, vol. 227, pp. 809-16, 2003, the disclosure of which are incorporated herein by reference. Fleischmann and Hittmair thus presented a scheme that attempted to adapt the administration of contrast agent into a biphasic injection tailored to the individual patient with the intent of optimizing imaging of the aorta. A fundamental difficulty with controlling the presentation of CT contrast agent is that hyperosmolar drug diffuses quickly from the central blood compartment. Additionally, the contrast is mixed with and diluted by blood that does not contain contrast.

Fleischmann proscribed that a small bolus injection, a test injection, of contrast agent (16 ml of contrast at 4 ml/s) be injected prior to the diagnostic scan. A dynamic enhancement scan was made across a vessel of interest. The resulting processed scan data (test scan) was interpreted as the impulse response of the patient/contrast medium system. Fleischmann derived the Fourier transform of the patient transfer function by dividing the Fourier transform of the test scan by the Fourier transform of the test injection. Assuming the system was a linear time invariant (LTI) system and that the desired output time domain signal was known (a flat diagnostic scan at a predefined enhancement level) Fleischmann derived an input time signal by dividing the frequency domain representations of the desired output by that of the patient transfer function. Because the method of Fleischmann et al. computes input signals that are not realizable in reality as a result of injection system limitations (for example, flow rate limitations), one must truncate and approximate the computed continuous time signal.

In addition to control of a powered injector to provide a desired time enhancement curve, the operation of a powered injector should be carefully controlled to ensure the safety of the patient. For example, it is desirable not to exceed a certain fluid pressure during an injection procedure. In addition to potential hazards to the patient (for example, vessel damage) and potential degradation of the diagnostic and/or therapeutic utility of the injection fluid, excessive pressure can lead to equipment failure. For example, because of the potential of cross-contamination between patients, the syringe and tubing used to carry fluid to a patient are typically changed on a per-patient basis. Such disposable syringes and other fluid path components (sometimes referred to collectively as a "disposable set") are typically fabricated from plastics of various burst strengths. If the injector causes pressure in the fluid path to rise above the burst strength of a disposable fluid path element, the fluid path element will fail.

In controlling system or injection pressure, many currently available injectors use motor current as an indirect indication of system pressure. This technique has inherent accuracy problems, as there are many variables between the parameter being measured (motor current) and the parameter of interest (fluid pressure). These include, for example, measurement inaccuracies, motor torque constant variation, motor variation with temperature, frictional effects in the drive train, and frictional effects in the syringe. In general, any control algorithm must allow for such errors and must make a conservative estimate of fluid pressure to prevent actual fluid pressure from reaching a hazardous value.

Many current systems typically predefine a conservative pressure control value. As the preset pressure control level (as, for example, determined by monitoring motor current) is reached, such injectors begin to slow down the flow rate of injection in an effort to stop the build up of pressure. At that point, an injector system that was originally intended to servo control the volume and flow rate of the injection fluid begins to servo control pressure. The inaccuracies inherent in using motor current to derive pressure result in a compliant system, and the operation of the servo in that state is oscillatory. Pressures in excess of desirable limits can occur, resulting in potentially hazardous operation of the injector.

In addition to problems of control with current injector systems, many such systems lack convenience and flexibility in the manner in which the injector systems must be operated. In that regard, the complexity of medical injection procedures and the hectic pace in all facets of the health care industry place a premium on the time and skills of an operator.

Pressure measurement in injection systems and pressure control and/or limitations are discussed, for example, in U.S. Pat. Nos. 5,808,203, 6,520,930 and 6,673,033, assigned to the assignee of the present invention, the disclosures of which are incorporated herein by reference. U.S. Pat. No. 6,520,930 discloses an injector control methodology which treats pressure as a hazard, rather than as a variable to be controlled. For example, a pressure hazard limit can be set as a trip point. When pressure in the system (as measured directly or indirectly) reaches the pressure hazard level, the injection may be terminated. The performance of the injector can be further limited in a manner to ensure that the user is not inconvenienced by continual shutdowns during normal operations. For example, the power delivered to the drive mechanism can be limited in a manner so that the pressure hazard limit or upper hazard level is not reached. In that regard, a pressure limit below the pressure hazard limit can be set such that power delivered to the drive mechanism is limited when the lower pressure limit is reached.

Although advances have been made in the control of fluid delivery systems to, for example, provide a desirable time enhancement curve and to provide for patient safety, it remains desirable to develop improved devices, systems, and methods for delivery of fluids to a patient.

SUMMARY OF THE INVENTION

In one aspect, the present invention provides a fluid injection apparatus including at least one pressurizing mechanism and at least a first fluid container (for example, a syringe or a bulk container) operably associated with the at least one pressurizing mechanism. The first fluid container is adapted to contain a first fluid to be injected. The fluid injection apparatus also includes a controller operably associated with the at least one pressurizing mechanism. The controller includes a programming system to allow programming of an injection protocol including, for example, a plurality of phases. At least one parameter generator is provided to determine parameters of at least one of the plurality of phases of the protocol based at least in part upon a type of the injection procedure.

As used herein with respect to an injection procedure, the term "protocol" refers to a group of parameters such as flow rate, volume injected, duration etc. that define the amount of fluid(s) to be delivered to a patient during an injection procedure. Such parameters can change over the course of the injection procedure. As used herein, the term "phase" refers generally to a group of parameters that define the amount of fluid(s) to be delivered to a patient during a period of time (or phase duration) that can be less than the total duration of the injection procedure. Thus, the parameters of a phase provide a description of the injection over a time instance corresponding to the time duration of the phase. An injection protocol for a particular injection procedure can, for example, be described as uniphasic (a single phase), biphasic (two phases) or multiphasic (two or more phases, but typically more than two phases). Multiphasic injections also include injections in which the parameters can change continuously over at least a portion of the injection procedure.

In several embodiments, the fluid injection apparatus further includes at least a second fluid container (for example, a syringe or a bulk container) operably associated with the at least one pressurizing mechanism. The second fluid container is adapted to contain a second fluid. The plurality of phases for the injection protocol can, for example, include at least one phase in which the first fluid is injected and at least one phase in which the second fluid is injected. The first fluid can, for example, be a contrast medium adapted to enhance contrast in a medical imaging system, and the second fluid can, for example, be a non-contrast-enhancing fluid. In several embodiments of the present invention the contrast enhancing agent or species in the contrast enhancing fluid is iodine or gadolinium. The non-contrast-enhancing fluid can, for example, be a flushing or diluent fluid such as saline.

The parameter generator can, for example, be adapted to generate parameters based upon at least one additional variable. The at least one additional variable can, for example, be a concentration of an enhancing species within the contrast medium or a patient specific physiological variable.

The parameters for each phase for each of the first fluid and the second fluid can, for example, include a volume to be injected and a flow rate profile for injection of the volume. The control system can, for example, provide a choice to an operator as to whether to program the parameters manually or to have the parameters programmed by the parameter generator. Moreover, parameters programmed by the parameter generator can, for example, be changed manually by an operator.

The operator can, for example, choose a type of injection procedure from a plurality of predefined types of injection procedures. In one embodiment, a graphical representation of regions of the patient is provided to an operator for selection of a region to be imaged. The selected region to be imaged can define the type of injection procedure. In another embodiment, a list of regions of a patient is provided to an operator for selection of a region to be imaged. The operator can also be provided with a choice of an algorithm from a plurality of algorithms adapted to be used by the parameter generator to generate the parameters.

In several embodiments of the present invention, at least one phase of the plurality of phases includes injection of an admixture of contrast enhancing fluid and non-contrast enhancing fluid.

The parameter generator can, for example, determine parameters for at least one phase at least in part on the basis of a test injection. In one embodiment, the parameter generator determines parameters for at least one phase (for example, an admixture phase) at least in part on the basis of time to peak enhancement determined in a test injection. For example, a ratio of contrast enhancing fluid to non-contrast enhancing fluid in an admixture phase can be determined by the parameter generator on the basis of time to peak enhancement. In one embodiment, a longer time to peak enhancement results in a higher ratio of contrast enhancing fluid to non-contrast enhancing fluid.

The fluid injection apparatus can also include a user interface system including an input mechanism via which an operator can input at least one of an input protocol or an output enhancement curve. The user interface system further includes a display. The fluid injection apparatus can also include at least one model adapted to provide at least one of a calculated output enhancement curve (for example, to be displayed on the display) if the user inputs an input protocol or a calculated input protocol (for example, to be displayed on the display) if the user inputs an output enhancement curve. The operator can, for example, draw the input protocol or the output enhancement curve on a component of the user interface system. In one embodiment, the operator draws the input protocol or the output enhancement curve on a component of the display of the user interface system.

In one embodiment, the concentration of an active agent present in the contrast enhancement fluid injected into the patient is decreased in or for at least one phase while flow rate of fluid injected to the patient is maintained generally constant (as compared to another phase). The concentration of an active agent present in the contrast enhancement fluid injected into the patient can, for example, be decreased continuously over a period of time while flow rate is maintained generally constant.

In several embodiments of the present invention, parameters are changed to effect enhancement of more than one region of interest over a duration of an imaging procedure. For example, parameters of at least one phase of the plurality of phases including injection of an admixture of contrast enhancing fluid and non-contrast enhancing fluid can be chosen to effect enhancement of more than one region of interest over a duration of an imaging procedure. In one embodiment, one region of interest is a left compartment of the heart and another region of interest is a right compartment of the heart. In another embodiment, one region of interest is a first portion of the liver and a second region of interest is another portion of the liver.

The fluid injection apparatus can also include a workflow system including a display setting forth graphically a representation of the steps required to initiate an injection procedure. The operator can, for example, select a step representation to complete ancillary operations required in the selected step. The display can, for example, set forth the graphical representation of the steps in a suggested sequential order.

The fluid injection apparatus can also include: a system for determining a pressure to be generated during at least one of the phases based upon at least one of the parameters of the phase. A mechanism can be provided to indicate if the pressure to be generated during the at least one of the phases is in excess of a pressure threshold.

In several embodiments, the programming system of the fluid injection apparatus includes a computer, and the parameter generator includes software stored in a computer memory (and executable by a computer).

In another aspect, the present invention provides an imaging system including an imaging device and a fluid injection apparatus as described above. The fluid injection apparatus can include at least one pressurizing mechanism and at least a first fluid container operably associated with the at least one pressurizing mechanism. The first fluid container is adapted to contain a first fluid to be injected. The fluid injection apparatus further includes a controller operably associated with the at least one pressurizing mechanism. The controller includes a programming system to allow programming of an injection protocol comprising a plurality of phases. At least one parameter generator is provided to determine parameters of at least one of the plurality of phases based at least in part upon a type of the injection procedure.

In another aspect, the present invention provides a method of delivering fluid to a patient including the steps: providing at least one pressurizing mechanism; providing at least a first fluid container operably associated with the at least one pressurizing mechanism, the first fluid container being adapted to contain a first fluid to be injected; providing a controller operably associated with the at least one pressurizing mechanism, the controller comprising a programming system to allow programming of an injection protocol comprising a plurality of phases; and determining at least one parameter of at least one of the plurality of phases via a parameter generator based at least in part upon a type of the injection procedure.

In a further aspect, the present invention provides a fluid injection apparatus including at least one pressurizing mechanism and at least a first fluid container operably associated with the at least one pressurizing mechanism. The first fluid container is adapted to contain a first fluid to be injected. The apparatus further includes a controller operably associated with the at least one pressurizing mechanism, which includes a programming system to allow programming of an injection protocol comprising at least one phase. The apparatus also include a system adapted to determine if a pressure to be generated during the least one phase exceeds a pressure threshold based upon at least one of the parameters of the phase. The apparatus can include a mechanism to indicate if the pressure to be generated during the at least one phase is in excess of the pressure threshold. The pressure system can be adapted to determine pressure at more than one point in a fluid path.

In another aspect, the present invention provides a fluid injection apparatus including at least one pressurizing mechanism and at least a first fluid container operably associated with the at least one pressurizing mechanism. The first fluid container is adapted to contain a first fluid to be injected via an injection fluid path. The apparatus further includes a pressure modeling system adapted to predict a pressure to be generated at at least one point in the injection fluid path during a planned injection procedure based upon variables associated with an injection protocol. The pressure modeling system can further include a mechanism adapted to determine if the predicted pressure exceeds a pressure threshold. The apparatus can also include a mechanism to indicate if the pressure to be generated is in excess of the pressure threshold. In one embodiment, the pressure modeling system is adapted to predict pressures to be generated at a plurality of points in the injection fluid path.

In a further aspect, the present invention provides a fluid injection apparatus including at least one pressurizing mechanism; at least a first fluid container operably associated with the at least one pressurizing mechanism, wherein the first fluid container is adapted to contain a first fluid to be injected; and a workflow system comprising a display setting forth graphically a representation of the steps required to initiate an injection procedure. The operator can, for example, select a step representation to complete ancillary operations required in the selected step. In one embodiment, the display sets forth the graphical representation of the steps in a suggested sequential order.

In still a further aspect, the present invention provides a fluid injection apparatus including at least one pressurizing mechanism; at least a first fluid container operably associated with the at least one pressurizing mechanism, wherein the first fluid container is to contain a first fluid to be injected; and a controller operably associated with the at least one pressurizing mechanism. The controller includes a programming system to allow programming of an injection protocol including at least one phase. The fluid injection apparatus further includes a user interface system including an input mechanism via which an operator can input at least one of an input protocol or an output enhancement curve. The user interface system further includes a display. The apparatus further includes at least one model adapted to provide at least one of a calculated output enhancement curve (for example, to be displayed on the display) if the user inputs an input protocol or a calculated input protocol (for example, to be displayed on the display) if the user inputs an output enhancement curve.

BRIEF DESCRIPTION OF THE DRAWINGS

FIG. 2 illustrates an embodiment of a graphical interface from which an operator can choose a vascular region of interest for imaging.

FIG. 25B is another portion or window of the graphical user interface of FIG. 25A.

DETAILED DESCRIPTION OF THE INVENTION

Figure 1:
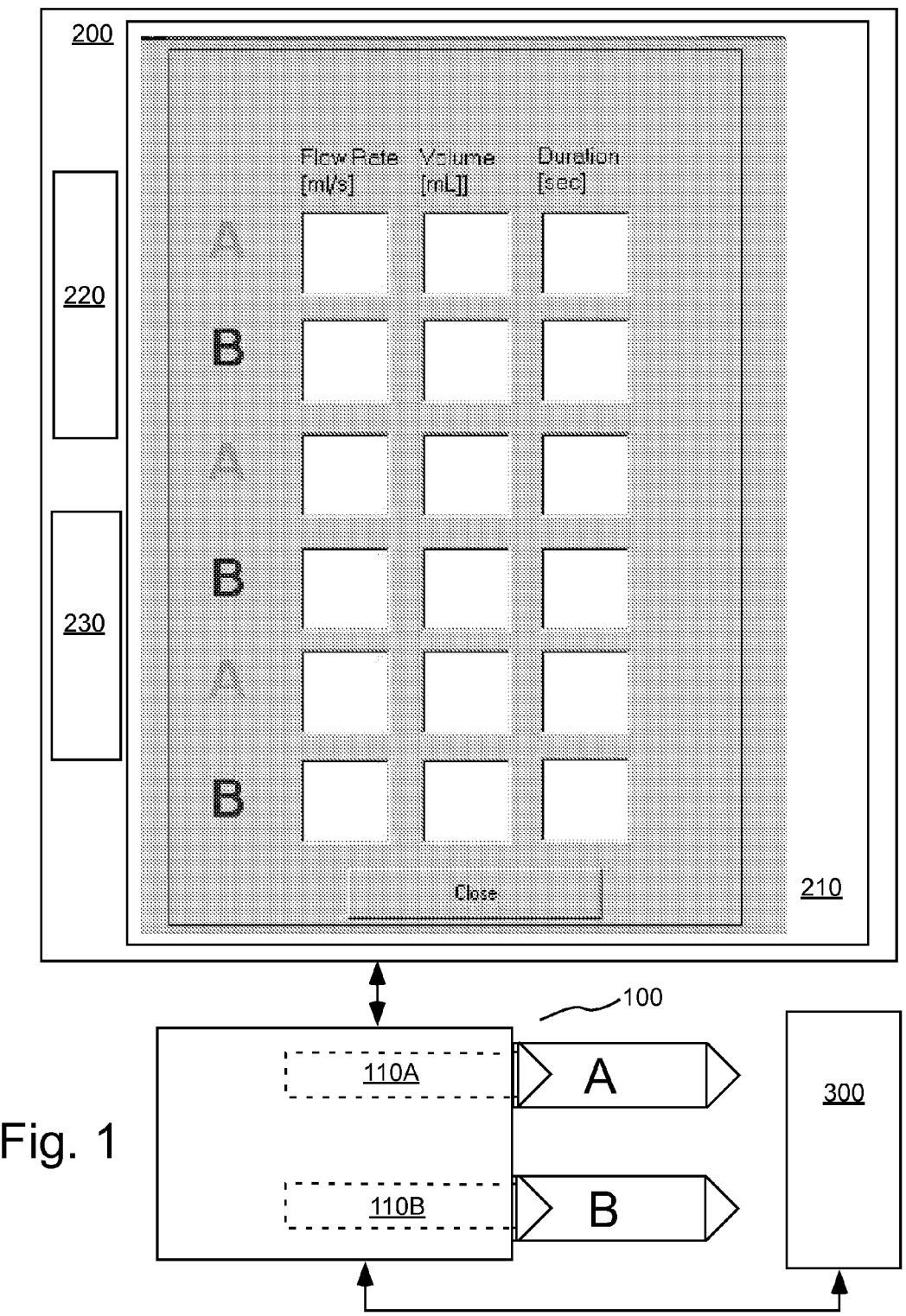
FIG. 1 illustrates an embodiment of a multi-phasic Graphical User Interface (GUI) for use in the present invention to set forth parameters for a plurality of phases for a two-syringe injector also illustrated in FIG. 1.

In several embodiments of the present invention, an injection system (such as a dual syringe injector system 100 as illustrated in FIG. 1 and as, for example, disclosed in U.S. Pat. No. 6,643,537 and Published U.S. Patent Application Publication No. 2004-0064041) for use with the present invention includes two fluid delivery sources (sometimes referred to as source "A" and source "B" herein; such as syringes) that are operable to introduce a first fluid and/or a second fluid (for example, contrast medium, saline etc.) to the patient independently (for example, simultaneously, simultaneously in different volumetric flow proportion to each other, or sequentially or subsequent to each other (that is, A then B, or B then A)). In the embodiment of FIG. 1, source A is in operative connection with a pressurizing mechanism such as a drive member 110A, and source B is in operative connection with a pressurizing mechanism such as a drive member 110B. The injection system includes a controller 200 is in operative connection with injector system 100. The controller 200 is operable to control the operation of drive members 110A and 110B to control injection of fluid A (for example, contrast medium) from source A and injection of fluid B (for example, saline) from source B, respectively. Controller 200 can, for example, include a user interface comprising a display 210. Controller 200 can also include a processor 220 (for example, a digital microprocessor as known in the art) in operative connection with a memory 230. An imaging system 300 (for example, a CT system, a Magnetic Resonance Imaging (MRI) system, an ultrasound imaging system, or a Positron Emission Tomography (PET) system can be in communicative connection with imaging system 300 and one, a plurality or all the components of the injection system and the imaging system 300 can be integrated.

In one embodiment of the present invention phase variables or parameters as described above are populated within a phase programming mechanism (see FIG. 1 for an embodiment of a user interface therefor that can, for example, be used with injector system 100) based on one or more parameters of interest, including, for example, but not limited to, contrast agent concentration (for example, iodine concentration in the case of a CT procedure), body weight, height, gender, age, the type of scan being performed, and the type of catheter inserted into the patient for intravascular access. As discussed above, differences in dosing requirements for different patients during imaging and other procedures have been recognized. For example, U.S. Pat. Nos. 5,840,026 and 6,385,483, assigned to the assignee of the present invention, the disclosures of which are incorporated herein by reference, disclose devices and methods to customize the injection to the patient using patient specific data derived before or during an injection. Likewise, PCT International Publication No. WO 2006/055813, designating the United States and claiming the benefit of U.S. Provisional Patent Application Ser. No. 60/628,201, assigned to the assignee of the present invention, the disclosures of which are incorporated herein by reference, also discloses customization of injections to a patient using patient specific data and sets forth a number of models to describe a time enhancement output for a given input or protocol.

Because optimal sets of flow rates and volumes are not readily known to the operator of the injector, the present invention eases the task of an operator in, for example, scanning patients in an imaging procedure by providing a set of injection protocols that are predetermined as being effective for the type of procedure being performed. For example, such protocols can be established in the clinical literature, established by collection of patient data over time (by, for example, employing artificial intelligence techniques, statistical means, adaptive learning methodologies etc.), established through mathematical modeling or otherwise established for a type of procedure being performed.

In one embodiment of the present invention, the operator first chooses the concentration of contrast agent (for example, concentration of iodine in a CT procedure) to be delivered into a patient. This choice is made, for example, by a selection mechanism, or by direct input of numerical values on the graphical user interface. The clinical operator can also select the gauge of the catheter inserted into that specific patient. Catheter size can be entered so that in subsequent steps, when the volumetric flow rate is determined, the pressure head to be developed in a disposable fluid path set can be calculated as described below (for example, via a computer program). Alternatively, one or more sensors can be provided to sense catheter size and provide this information to the injector.

The clinical operator can, for example, control the injection system by either entering volumes and flow rates manually into the fields provided on the User Interface (see FIG. 1) or by entering a "protocol wizard mode", "helper mode" or "operator assist mode", as described herein, wherein such fields are automatically populated. If the operator chooses to enter the operator assist mode, the operator can be presented with a mechanism or mode (see, for example, FIG. 2) of selecting an organ or vascular system to be scanned The present invention provides systems, devices and methodologies or algorithms that predict the flow rate profile (which can be constant during a phase or varying) and volume of contrast agent to deliver depending upon the procedure and the region of interest chosen. For example, an operator can choose the heart, descending aorta or ascending aorta (referred to as cardiac imaging, a form of Computed Tomography Angiography (CTA)). One embodiment of a graphical interface from which the operator chooses the vascular region of interest, and which follows the work flow described herein, is depicted in FIG. 2. The operator can, for example, choose a region of interest by highlighting (for example, using a touch screen or a mouse controlled cursor) a region of interest on an illustration of the body set forth on the user interface or can choose a region of interest from a menu such as a pull down menu. Hierarchical groupings of regions of interest can be provided.

Figure 3:
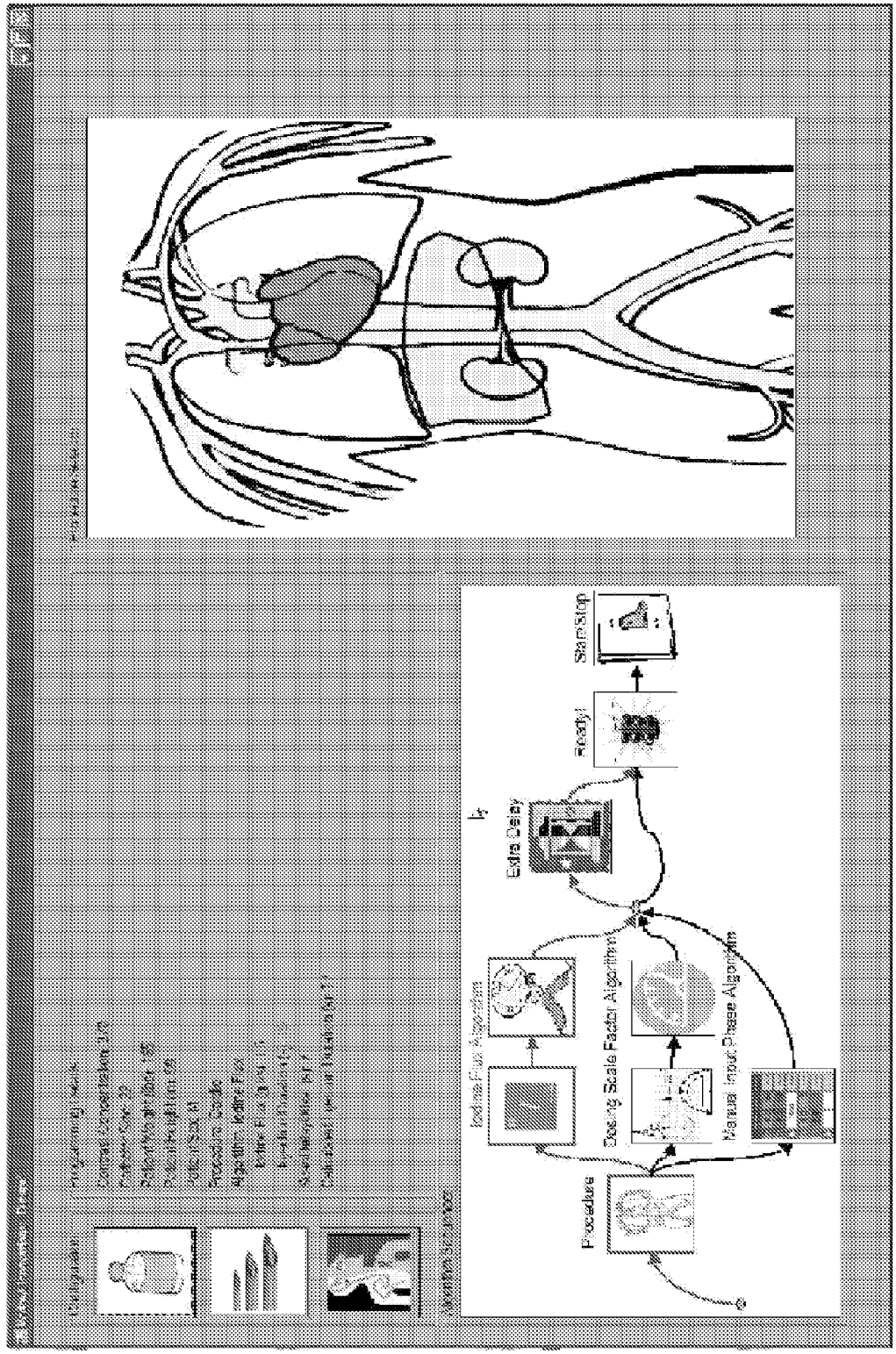
FIG. 3 illustrates an embodiment of a graphical interface of a proposed work flow environment for use in the present invention.

Upon choosing the region to be imaged, the operator can, for example, be prompted to enter values for other variables (for example, patient physiological variables such as the patient's weight, height, gender etc.). An example of an embodiment or implementation of this is to provide a keypad on the user interface into which the operator enters the patient's weight in pounds or kilograms. In another embodiment, the operator chooses a weight range from among low, mid and high ranges. Such variables can also be measured by one or more sensing devices associated with the system and/or read electronically or digitally from patient records as may be kept in a hospital database. The steps necessary to conduct a contrast injection can be presented to the operator as depicted in FIG. 3. In the embodiment of FIG. 3, the operator can, for example, be prompted in an order (for example, a suggested or required sequential order) natural to the type of imaging procedure to be performed. The operator can, for example, be given the ability to choose a vascular region or organ of the body to image, the type of algorithm to conduct the injection, and an ability to change the type contrast, catheter gauge, and physical attributes of the patient.

Figure 4:
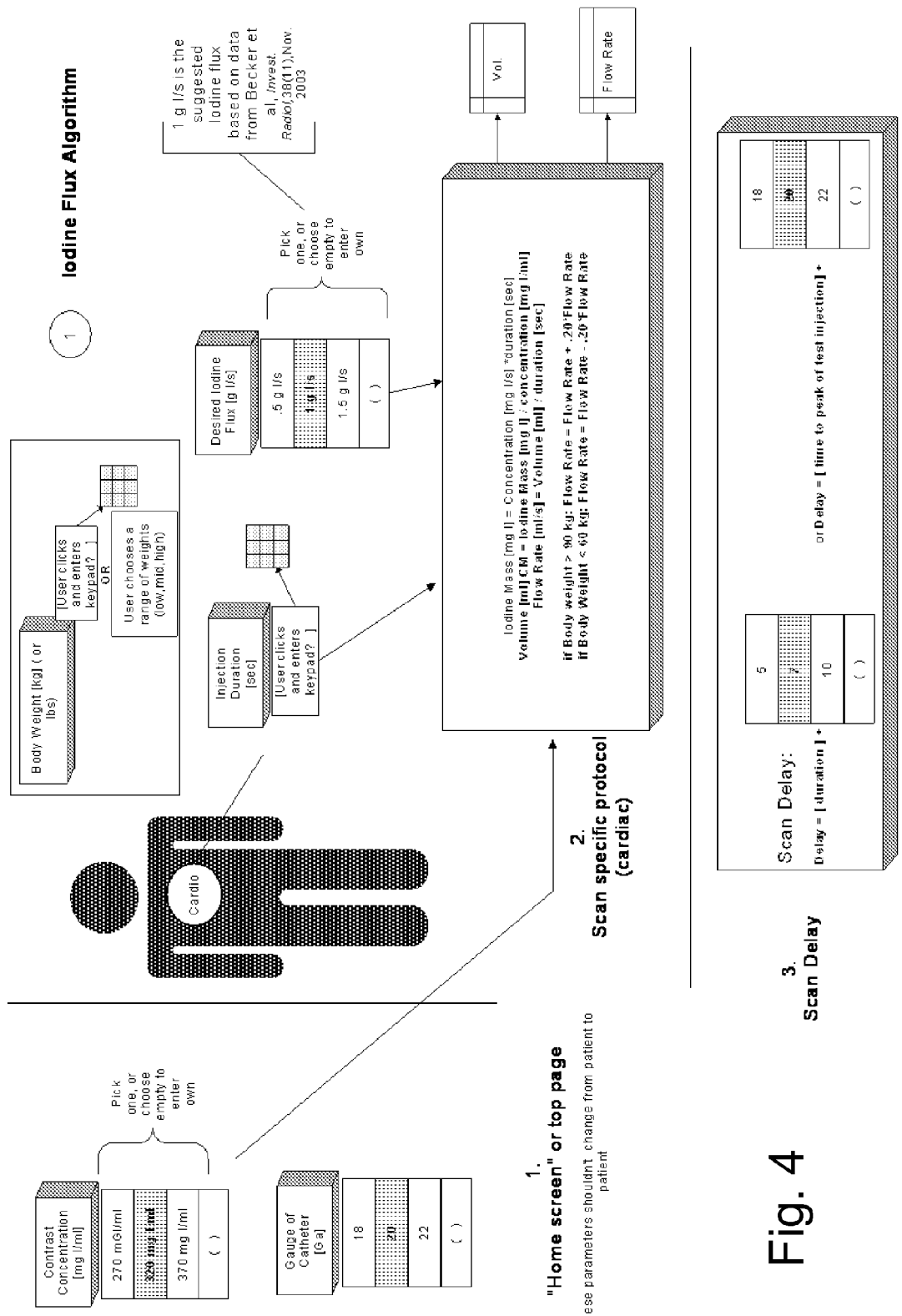
FIG. 4 illustrates an embodiment of an iodine flux algorithm for use in the present invention.
Figure 5:
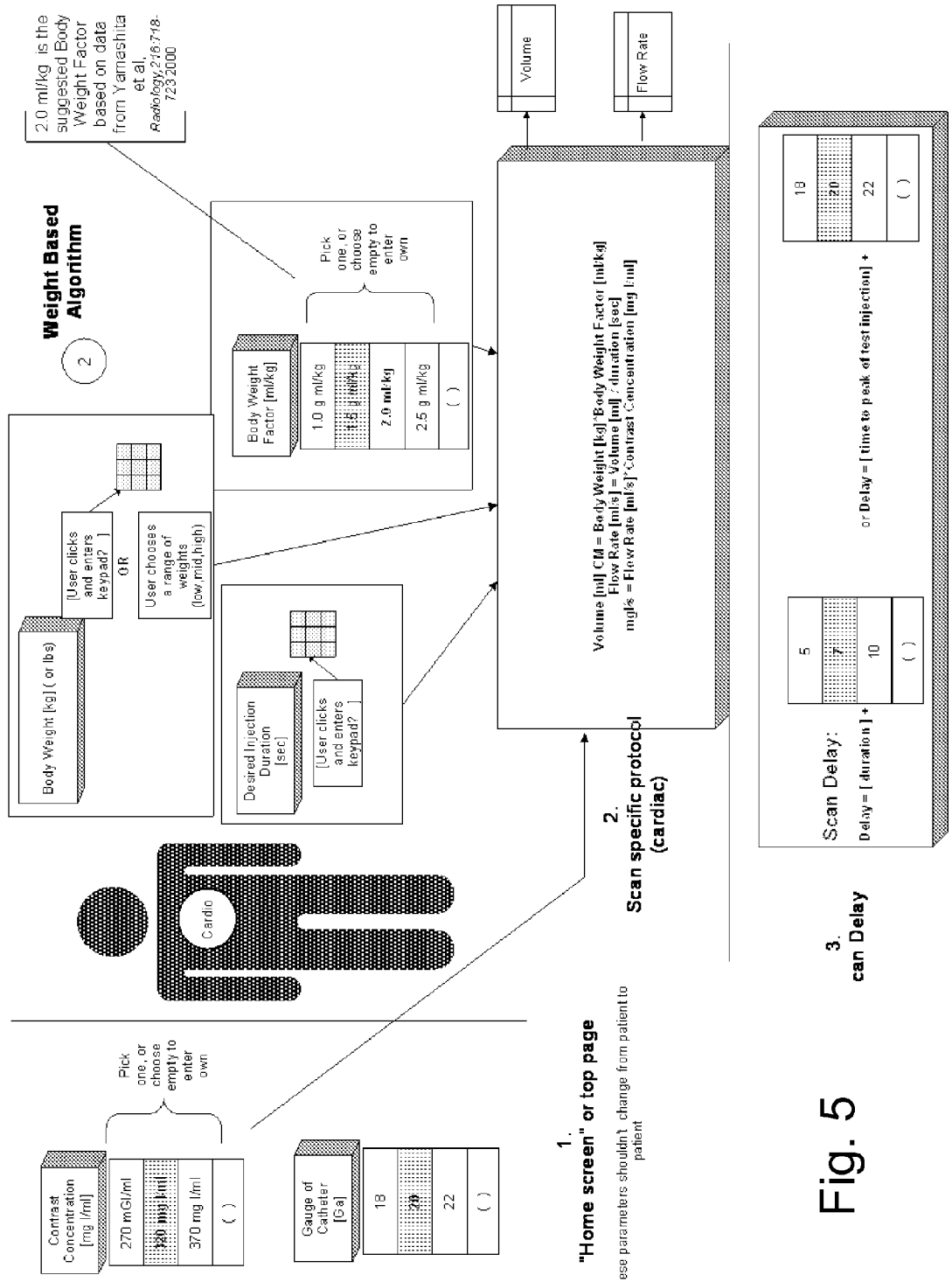
FIG. 5 illustrates an embodiment of a weight based algorithm for use in the present invention.
Figure 6:
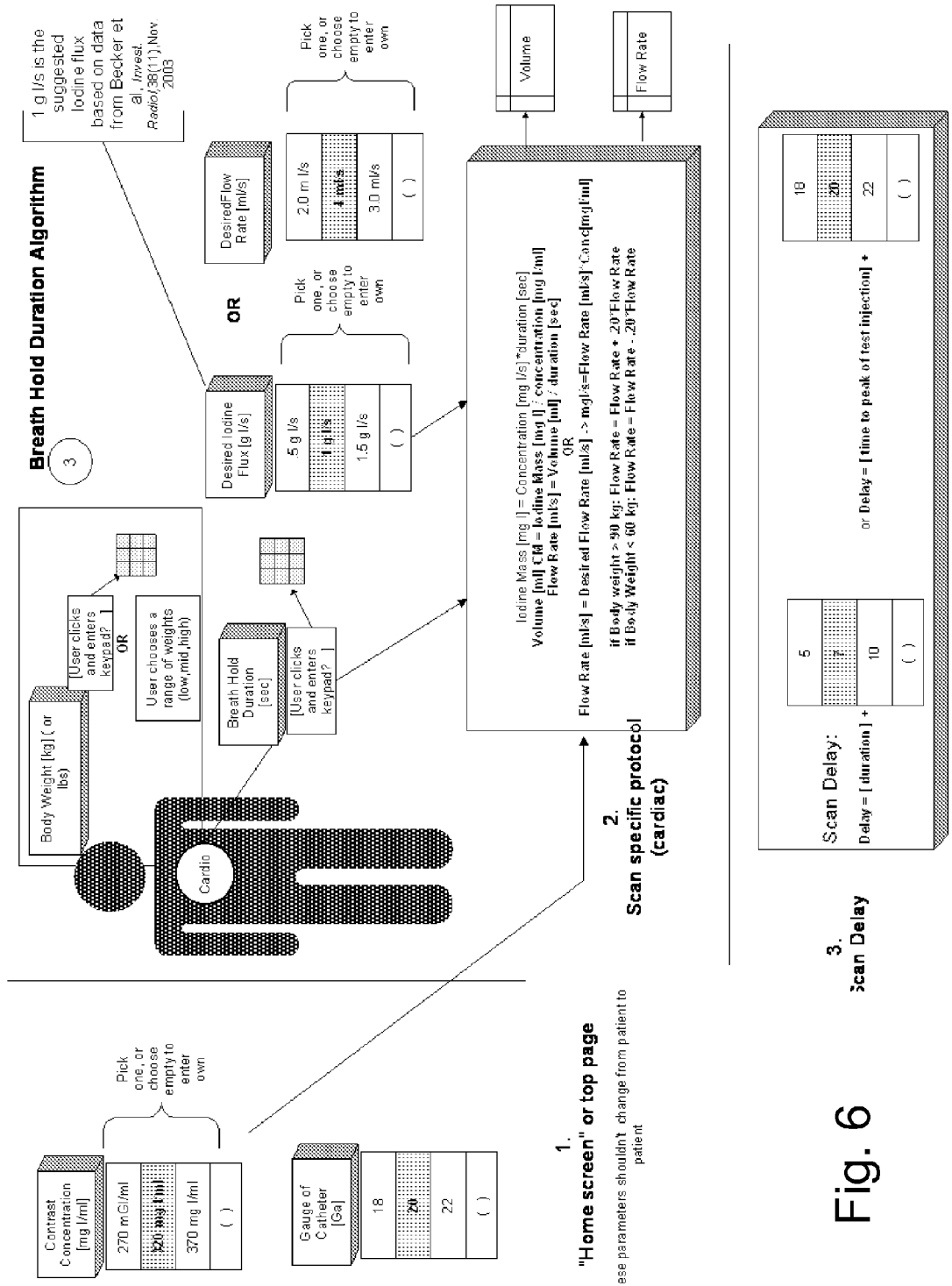
FIG. 6 illustrates an embodiment of a breath hold duration algorithm for use in the present invention.

As discussed above, the operator can be presented with a choice of the type of algorithm the operator would like the system to use to produce a set of flow rates and volumes (that is, phase parameters) for that patient. In the case of cardiac imaging, algorithm choices can, for example, include: (i) an Iodine Flux Algorithm, (see FIG. 4) (ii) a Weight Based Algorithm (see FIG. 5), or (iii) a Breath Hold Duration Algorithm (see FIG. 6). Each of these algorithms can, for example, be based upon empirical data (for example, as published in the radiological medical literature). Additional algorithms can be included for other types or classes of imaging procedures. The methodology and/or logic for an embodiment of the three algorithms described above is set forth in FIGS. 4 through 6, respectively. Upon entering the data required for a particular algorithm, the operator can be queried if the operator wishes to perform a test injection (or timing injection). If the operator chooses yes, the software can provide that, for example, two additional phases (corresponding to the test injection) must be inserted in the start of the injection protocol (for example, one phase for contrast delivery and a subsequent phase for a saline flush injection).

Based upon the selections made, the software implementing the present invention computes an injection protocol for the user's review. If the operator chooses to perform a test-injection, then the first two phases of the protocol can, for example, include injection of 15 or 20 ml of contrast agent (for example, 15 ml if the patient weight<90 kg, 20 ml >90 kg) delivered at 4 ml/s. The second phase of the protocol can include injection of 20 ml of saline injected at 4 ml/s. The next phase or phases can, for example, include volumes and flow rates computed by one of the three algorithms discussed above in connection with FIGS. 4 through 6.

In one embodiment of the present invention, injection parameters for an injection procedure, including a phase in which an admixture of contrast media and a diluent/flushing fluid (for example, saline) are calculated. In that regard, to address a number of problems associated with, for example, heart imaging procedures have been developed which include the injection of saline following the contrast agent bolus, and, more recently, the admixture of contrast media with saline via simultaneous injection of contrast media and saline (sometimes referred to herein as "dual flow").

As discussed above, Bae et al. have proposed a solution to the non-uniform enhancement problems by suggesting that one inject contrast with an exponentially decaying flow rate over time. While this technique can indeed produce more uniform contrast enhancement in a large vessel, it also reduces the maximum enhancement, which is not necessarily desirable. Bae, K. T., H. Q. Tran, et al. (2004). "Uniform vascular contrast enhancement and reduced contrast medium volume achieved by using exponentially decelerated contrast material injection method." Radiology 231(3): 732-6. While, theoretically, it seems logical to believe that the exponentially decaying flow rates can help with right-heart artifacts (for example, by introducing less contrast later in the injection and mixing less with the earlier injected contrast), it has not been demonstrated or investigated. Furthermore, because the latter portion of the decayed injection is at a lower flow rate, there is a loss of momentum for that section of the bolus, slowing its entry to the right heart. While a saline push after the decayed exponential injection may help in ensuring the contrast is all "pushed" into the right heart, turbulence resulting from the mixing of contrast and blood at different flow rates may cause flow artifact within the right heart.

An alternative for reducing right heart artifact is to inject a volume of contrast at a discrete flow rate followed by an admixture of contrast and saline (with a final push of saline). The admixture can be injected at the same flow rate as the initial bolus of contrast. The admixture can be produced by the simultaneous injection of contrast and saline with, for example, a dual-syringe power injector; wherein the flow rates of contrast and saline are proportional to each other. This technique has been recently adopted in the clinical setting and initial results are suggesting that it reduces right heart artifact. See Sablayrolles, J. (2004). "Cardiac CT:Experience from Daily Practice." Advanced CT August 4-10. However, in implementing such admixture protocols, there are currently no established systems or methods for determining appropriate or ideal injection parameters for a given patient (for example, initial flow rate and volume, percentage of admixture, duration of the phases, and scan delay).

In one embodiment, the present invention provides systems and methods for interfacing with the injection system to reduce clinician "guesses" at appropriate or optimal flow rate and volume parameters for a given patient. The systems and methods of the present invention provide for the consideration of a number of variable including, but not limited to, patient specific parameters such as patient weight (and other habitus indicators), time of contrast arrival from a timing injection, contrast concentration, and total desired contrast agent (for example, iodine) load. The systems and methods of the present invention can, for example, include a per-patient saline admixture protocol generator.

Figure 7:
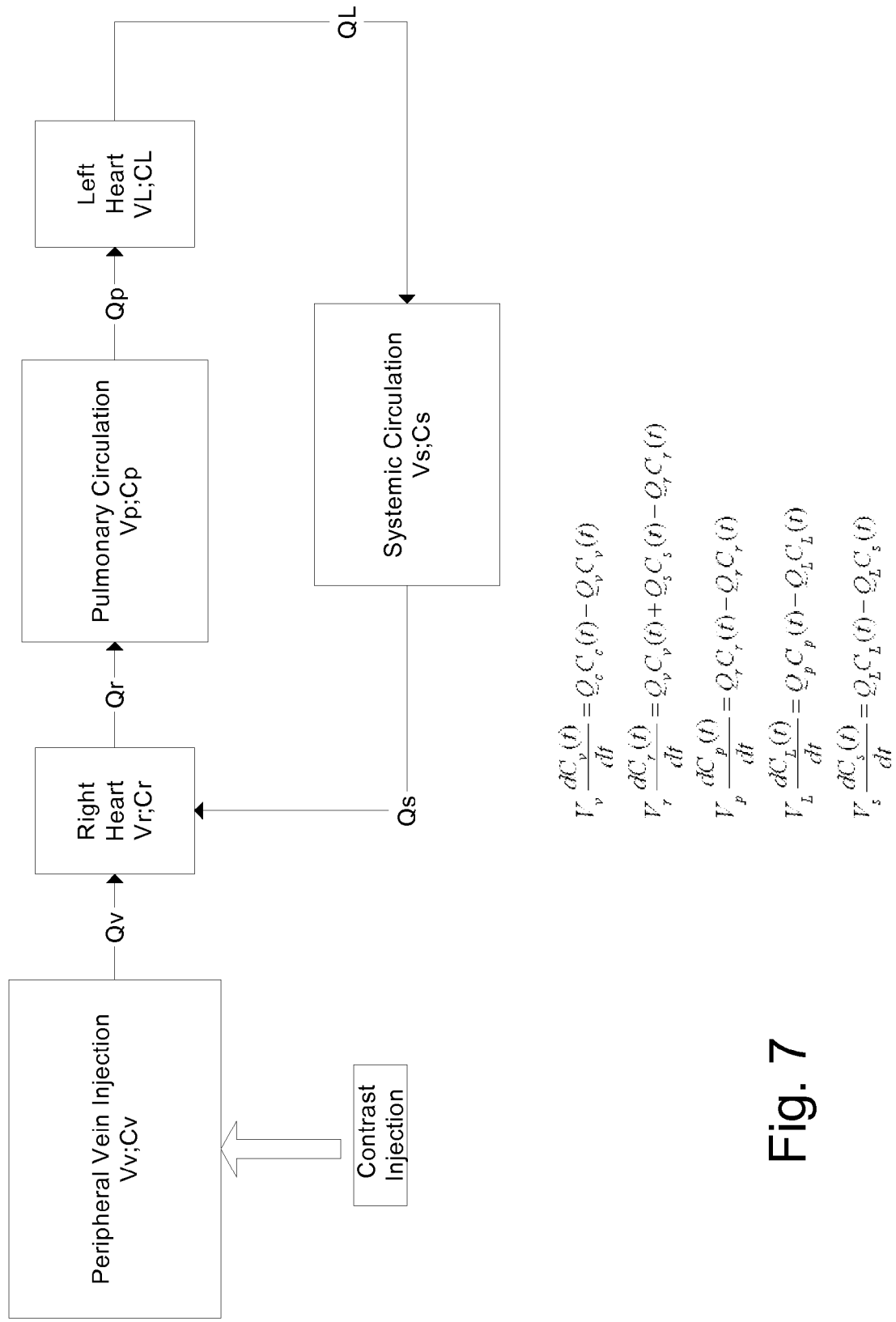
FIG. 7 illustrates an embodiment of a reduced-order compartmental model and the first-order coupled differential equation system describing this model.

The predicted contrast enhancement in the aortic/heart compartment of a human male can be used in this section to elaborate the principle of the proposed algorithm. Simulations were performed in a SIMULINK® (available from MathWorks, Inc. of Natick Mass.) implementation of a reduced-order PK model as described in Bae et al. See Bae, K. T., J. P. Heiken, et al. (1998). "Aortic and hepatic contrast medium enhancement at CT. Part I. Prediction with a computer model." Radiology 207(3): 647-55 and Bae, K. T., H. Q. Tran, et al. (2000). "Multiphasic injection method for uniform prolonged vascular enhancement at CT angiography: pharmacokinetic analysis and experimental porcine model." Radiology 216(3): 872-80, U.S. Pat. Nos. 5,583,902, 5,687,208, 6,055,985, 6,470,889 and 6,635,030. The modeling approach in that work recognized that the full body physiologic pharmacokinetic model taught in Bae, Heiken et al, 1998 supra, was too large and included too many unknowns to feasibly compute on a per patient basis. Bae and colleagues, therefore, approximated large parts of the anatomy with single compartments and, because first-pass enhancement dynamics are of interest, removed the capillary transfer compartments. The resulting, reduced-order model is illustrated in FIG. 7. In FIG. 7, V are the fluid volumes of the respective "compartments", C are the predicted concentrations in each "compartment", and Q are the volumetric flow rates of blood throughout the body. Q and V are estimated from anatomical data. The first-order, coupled differential equation system describing this model is formulated assuming a continuous time process and is also set forth in FIG. 7.

Figure 8A:
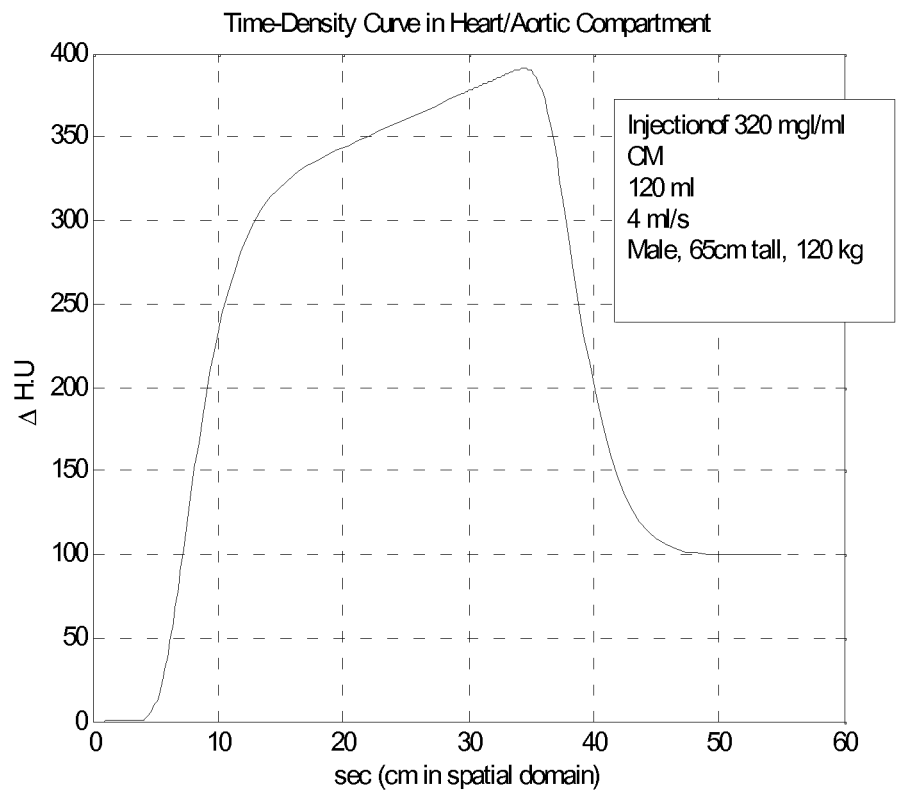
FIG. 8A illustrates a simulated enhancement curve in the heart/aortic compartment of a 65 cm, 120 kg male.
Figure 8B:
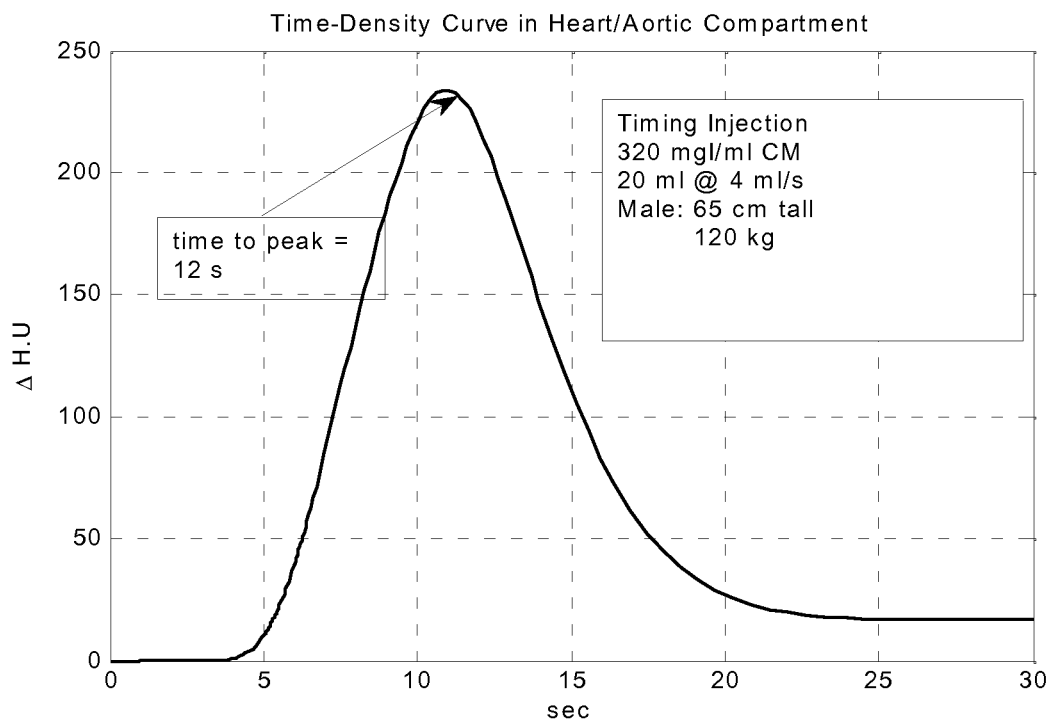
FIG. 8B illustrates an enhancement curve to a test/timing injection from the simulated patient in FIG. 8A.
Figure 9:
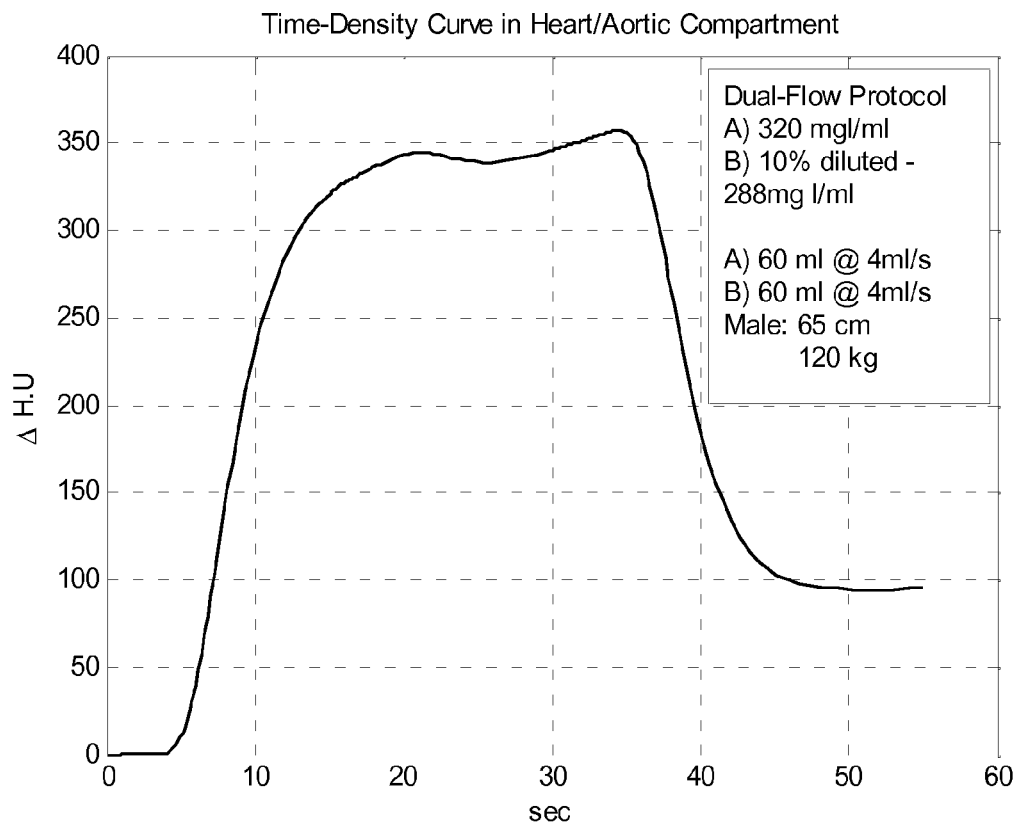
FIG. 9 illustrates a simulated enhancement curve for the simulated patient of FIG. 8A using the proposed methodology described within.

In several studies of the present invention, an assumption was made that the aortic/heart compartment was well mixed. Although the x-axes in FIGS. 8A through 9 are labeled in time units, another assumption was that the time axis maps to spatial dimensions in the compartment of interest. FIG. 8A demonstrates the phenomenon of non-uniform contrast enhancement (caused by recirculation of contrast into the compartment). FIG. 8B presents the results of performing a small volume "test" or "timing" injection on the same patient scanned in connection with FIG. 8A (the cardiac output and central blood volume for the model were derived from anthropometric data tables). The time to peak contrast enhancement was measured as 12 seconds in FIG. 8B. The time of peak represents the transit time for a small bolus of contrast to migrate from the injection site, to the right heart, through the pulmonary circulation, and to the left heart compartment. The simulated time to peak enhancement may be less than that from a "real" patient. In that regard, the Bae model set forth in FIG. 7 was not directly validated with human data, but was allometrically scaled from porcine data. In any event, the absolute values in these simulations are not critical. Rather, we are interested in the dynamics of the system. Noticeable in FIG. 8B is the recirculation of contrast after the peak (or first moment) of the bolus arrived in the compartment (>15 sec). The reduced-order model set forth in FIG. 7 does not reproduce with high fidelity the recirculation dynamics (for example secondary peaks).

Bae et al. concluded that if an injection duration is longer than the time for contrast arrival as computed from a timing injection, that the time to peak contrast enhancement increases linearly as the duration of injection increases. As the duration of the injection exceeds the duration of the time to peak of the test injection, the asymmetry of the enhancement curve becomes pronounced because the new contrast is mixing with the contrast already present in the compartment. This phenomenon serves as a basis of one embodiment of one algorithm of the present invention for computing admixture protocol (for example, saline plus contrast media).

FIG. 9 sets forth a time enhancement curve that was simulated with a biphasic protocol. The first phase's duration was computed to equal the time to peak enhancement of the timing bolus, plus three seconds (an arbitrary offset term). The second phase was a diluted phase (90% contrast, 10% saline) that resulted in an effective contrast concentration of 288 mgI/ml (concentration in the dilution phase=desired or programmed ratio (90/100 in this instance)*concentration of drug (320 mgI/ml)). The volume was set so that a total volume of 120 ml was injected into the patient. The flow rate was the same in both phases to maintain the momentum of the contrast into the right heart. FIG. 9 demonstrates a reduction in the asymmetric "peak" in the second half of the injection, while maintaining a contrast enhancement about 350 HU. In comparison, the exponentially decreasing flow rate technique recommended by Bae et al. results in a lower peak enhancement. An advantage of the injection protocol of the present invention (as compared to a decelerating injection flow rate protocol) arises in that, because the volumetric flow rate of the injected fluid is not decreasing, there is less likelihood for flow artifacts within the peripheral venous system before the heart. In that regard, injectate moving with a flow rate less than the endogenous flow rate of the venous system can result in dispersion of the contrast media because some parts of the bolus arrive to the right heart with different velocities. In the present invention, a multiphasic injection protocol can be provided in which one or more of the parameters are changed periodically or continuously over at least a period of the injection duration, wherein total flow rate is maintained constant. In this manner, for example, a concentration of contrast active agent (for example, iodine, gadolinium etc.) delivered to a patient can be decreased over time while maintaining flow rate constant (for example, by increasing the portion of saline injected during that time). A broader, more uniform peak of enhancement can thereby be maintained (see, for example, FIG. 9). Moreover, that uniformity can be changed between different phases of the injection procedure. For example, liver enhancement can be changed during different phases of the imaging procedure to, for example, correspond to different portions of the liver in which peak enhancement time can vary because of variations in blood supply.

Another embodiment of the present invention for protocol determination in the case of a dual flow injection or simultaneous injection of an admixture of diluent/flushing fluid and contrast is discussed in connection with FIGS. 10 through 18. Once again, a primary goal of rational CT contrast protocol design is to develop injection protocols tailored to each patient considering, for example, the individual's hemodynamic state, the imaging region of interest, and the injection system constraints. The injection strategy can, for example, make use of the ability of the Stellant D injection system, available from Medrad, Inc. of Indianola, Pa., to provide simultaneous delivery (and thus dilution) of contrast media and saline. As described below, an additional phase of diluted contrast media allows for additional left heart enhancement, but with a reduced contrast agent (iodine) load to reduce or eliminate right heart artifacts.

Figure 10:
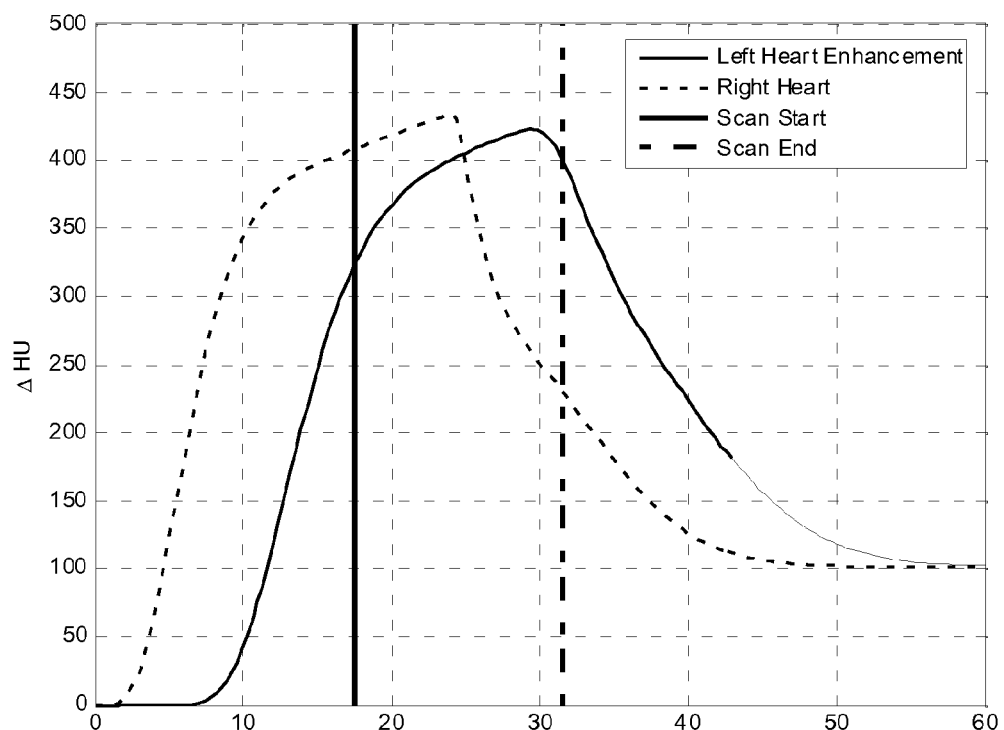
FIG. 10 illustrates a time enhancement curve resulting from a 120 ml uniphasic injection.
Figure 11:
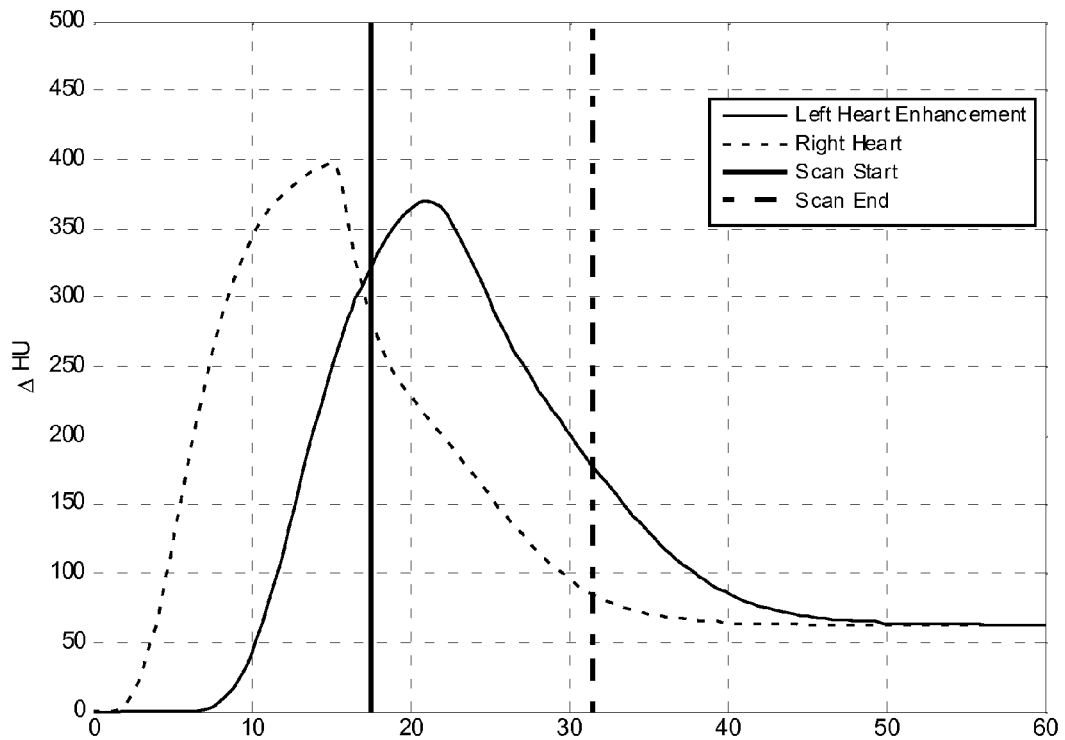
FIG. 11 illustrates a time enhancement curve resulting from a 75 ml contrast bolus followed with a 50 ml saline push or flush.

FIGS. 10 through 14 illustrate enhancement profiles (simulated as described above) for a 35 yr old, healthy male (200 lbs, 6 ft tall) injected with 370 mgI/ml contrast medium. Enhancement curves are presented for the right heart and the left heart compartments as predicted with the compartmental, pharmacokinetic model set forth in FIG. 7. FIG. 10 depicts enhancement with a 120 ml uniphasic injection, whereas FIG. 11 presents the enhancement resulting from a 75 ml bolus followed with a 50 ml saline push or flush. Whereas the enhancement of the left heart in FIG. 10 is above 300 Hounsfield Units (HU) throughout the scan duration, the right heart is enhanced brightly throughout the scan window, and is more likely to produce image artifacts.

Figure 12:
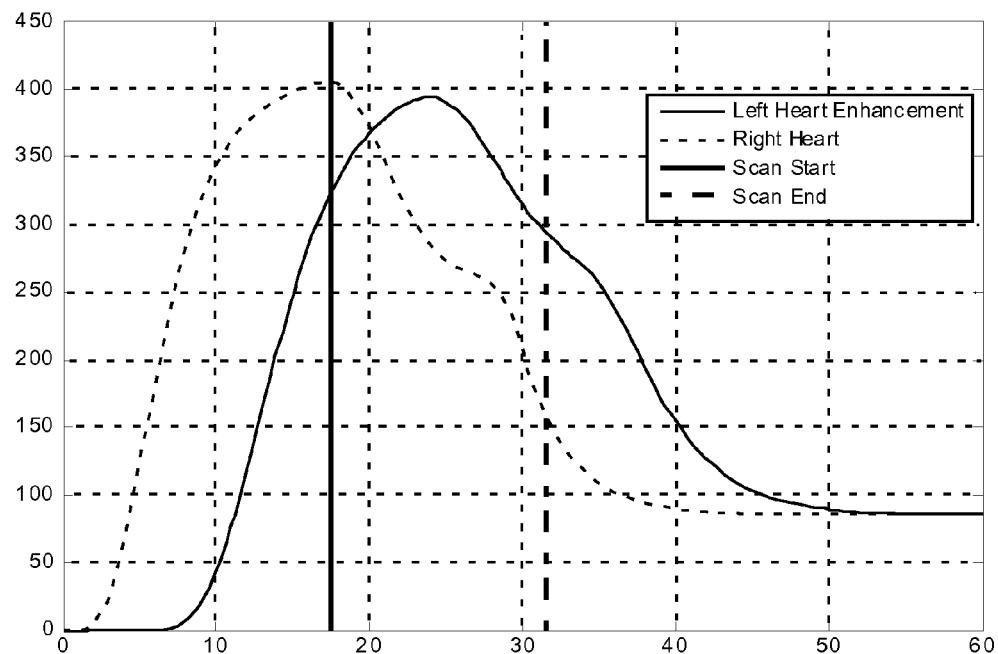
FIG. 12 illustrates simulated time enhancement curves resulting from injections performed with a 75 ml main bolus followed by a diluted phase of contrast of the same flow rate having a contrast/saline ratio of 50/50.
Figure 13:
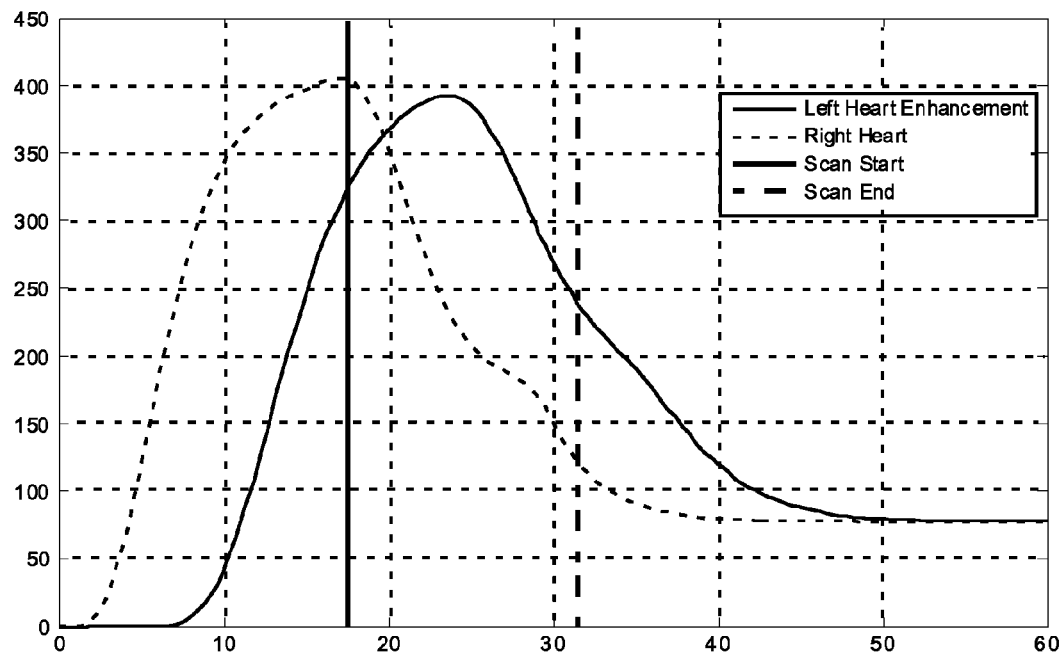
FIG. 13 illustrates simulated time enhancement curves resulting from injections performed with a 75 ml main bolus followed by a diluted phase of contrast of the same flow rate having a contrast/saline ratio of 30/70.
Figure 14:
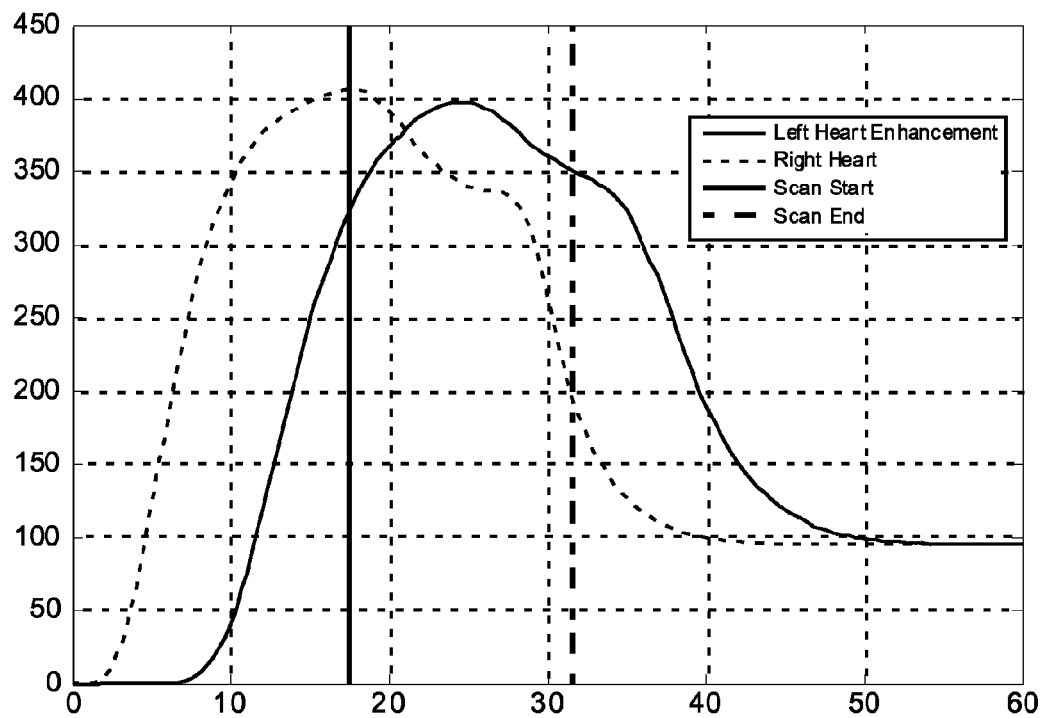
FIG. 14 illustrates simulated time enhancement curves resulting from injections performed with a 75 ml main bolus followed by a diluted phase of contrast of the same flow rate having a contrast/saline ratio of 70/30.

FIGS. 12-14 illustrate simulated time enhancement curves resulting from injections performed with a 75 ml main bolus followed by a diluted phase of contrast of the same flow rate in the following contrast/saline ratios: 50/50, 30/70, and 70/30, respectively. The enhancements of the left and right hearts were clearly modified by the additional phase of diluted contrast. The 70/30 phase (FIG. 14) provided good left heart enhancement, but the right heart enhancement may have been too great. The 30/70 ratio (FIG. 13) provided good right heart enhancement, but not enough left heart enhancement throughout the scan window. The 50/50 ratio (FIG. 12) provides the best trade-off, for this simulated patient, of right heart and left heart enhancement.

Figure 15:
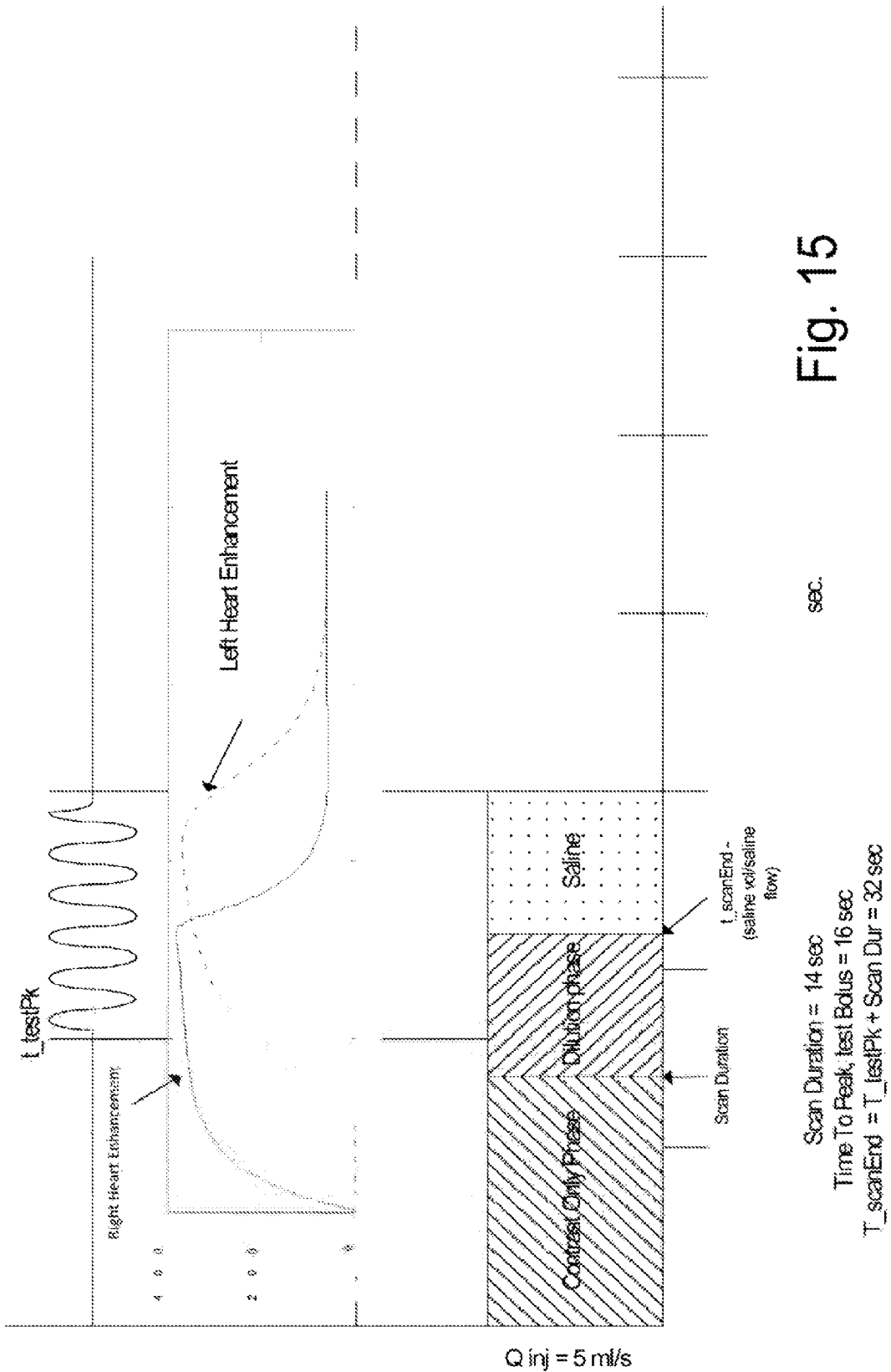
FIG. 15 illustrates an injection process of contrast material with a fixed, time axis wherein the bottom axis presents the contrast injection profile, the middle axis sets forth the enhancement profiles for left and right heart compartments, and the top axis sets forth the scanning duration.

FIG. 15 illustrates an injection process of contrast material with a fixed, time axis. The bottom axis presents the contrast injection profile (in this instance, a uniphasic injection at 5 ml/s), the middle axis sets forth the enhancement profiles for left and right heart compartments, and the top axis presents the scanning duration. The two vertical lines represent the start and completion times of the scan. In one embodiment, an algorithm of the present invention assumes that the clinician performs a small, test bolus injection of contrast (for example, a test injection of 20-25 ml of contrast at the same flow rate as the flow rate to be used during the diagnostic scan) followed by a saline push. A dynamic CT scan generates an enhancement curve from which the time to peak of the test bolus and the enhancement peak of the test bolus can be measured/recorded. It is also assumed that the scan duration is known before the test bolus and diagnostic injections begin.

The first bolus of contrast is made equal in duration to the scan duration. The flow rate is given by the operator (assumed to be 5 ml/s in this study). The volume of the first phase, therefore, is the product of scan duration and flow rate. The determination of the volume of the second phase is made by considering the time to peak of the test injection, the duration of the first phase, and the end of the scan. The contrast injection should not last longer than the end of the scan. Because of the propagation delay of contrast from the injection site to the right atrium (about 5-8 seconds typically), contrast injection is stopped 5-8 seconds before the end of the scan so that the follow on contrast can fill the right heart. The approach taken in connection with the embodiment of FIG. 15 proscribed a saline flush of 40 ml at 5 ml/s, so we ended the contrast injection of the dilution phase 8 seconds before the end of the scan.

The volume of the second, diluted phase is then determined by:

$$Vol_2 = \left(\left(t_{scan\_end} - \frac{40 \text{ ml}}{5 \text{ ml/s}}\right) - duration_1\right) \cdot 5 \text{ ml/s}$$

The value $T_{scan\_end}$ is computed by consideration of the time to peak of the test bolus and the scan duration:

$$t_{scan\_end} = t_{test\_bolus\_peak} + duration_{scan}$$

Figures 16, 17:
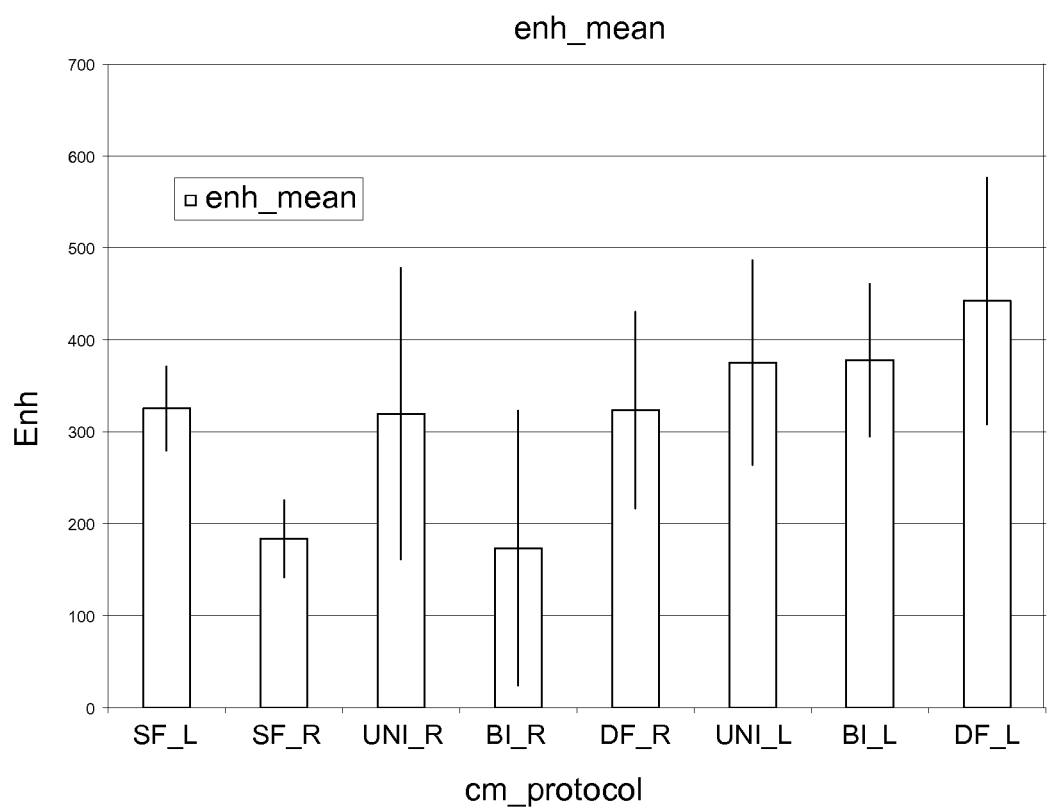
FIG. 16 illustrates a heuristic for determining contrast/saline ratio of an admixture or dual flow phase on the basis of peak enhancement of a test bolus.
FIG. 17 sets forth preliminary clinical data for uniphasic injections, biphasic injections and multiphasic, admixture injections of the present invention.

The ratio of the second phase is determined by a heuristic that maps peak enhancement of the test bolus to contrast/saline ratio as set forth in FIG. 16.

To limit the total amount of contrast delivered to each patient (in the event of an extremely long time to peak of the test enhancement), a maximum of 40 ml is made available for the dilution phase. If the computations above suggest a contrast volume greater than 40 ml., the system can limit the total contrast volume to 40 ml, compute the total volume in that phase (with the saline) considering the dilution ratio so as not to exceed 40 ml of contrast. The total contrast volume allowable in the dilution phase can also be set as a function of weight, estimated cardiac output, Body Mass Index, or other physiometric indicator.

The threshold values in FIG. 16 were determined by analyzing clinical data from a sample of 50 test bolus injections and subsequent numerical modeling. Heuristically, the rule is designed to provide more contrast in patients with smaller peak enhancements (assuming that more contrast is needed for sufficient left and right heart enhancement) and less contrast to patients with strong test enhancements. Because the volume of agent is being tailored to patients with longer or shorter times to peak, and the total iodine load is adjusted based on test bolus enhancement, variability among patient enhancement should be reduced with this approach. FIG. 17 sets forth preliminary clinical data indicating this outcome. In FIG. 17, the first 2 bars are data generated with the algorithm just described for the left and right heart (SF_L and SF_R, respectively). The error bars indicate +/−1 standard deviation. The remaining data points are enhancement values generated with a uniphasic protocol of 120 ml of contrast (350 mgI/ml, no saline push; UNI_R and UNI_L), a biphasic protocol (75 ml of 350 mgI/ml with 40 ml of saline; BI_R and BI_L), and finally a dilution protocol with a fixed dilution ratio of 30/70 for all subjects (initial phase volume of 350 mg I/ml=scan duration*5 ml/s; DF_R and DF_L). The volume of the second phase was a fixed 50 ml of fluid. A saline flush of 40 ml followed).

Figure 18:
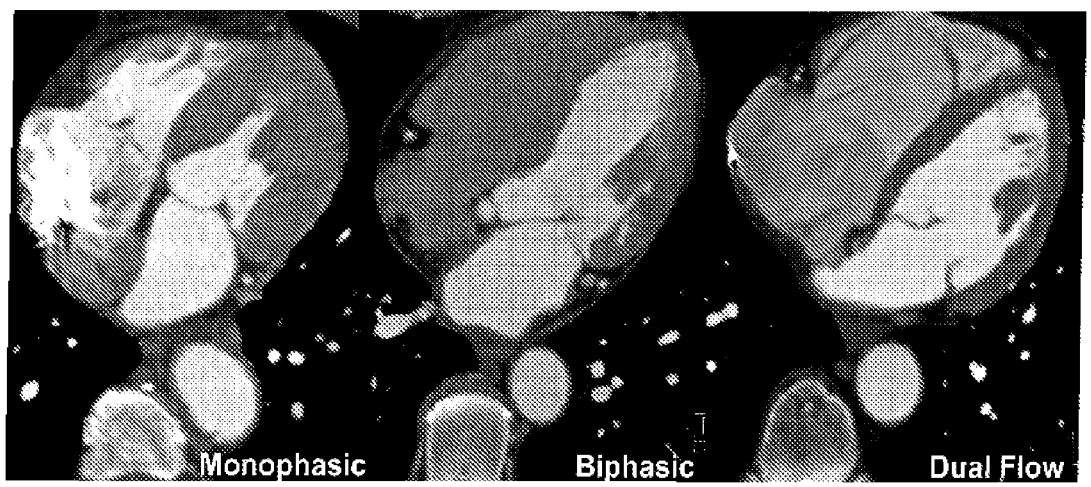
FIG. 18 illustrates several scan images of the left and right heart for a uniphasic injection, a biphasic injection and a multiphasic injection including a phase in which a contrast/saline admixture is injected.

FIG. 18 sets froth scan images for the left and right heart in the case of a uniphasic or monophasic injection protocol (contrast only, no saline flush), a biphasic protocol (contrast followed by a saline flush) and a dual flow injection protocol as described above (contrast, followed by a contrast/saline admixture, followed by a saline flush). As illustrated in FIG. 18, a dual flow injection procedure in which the injection protocols can be determined as described above can provide improved imaging procedures for the left and right heart.

Figure 19:
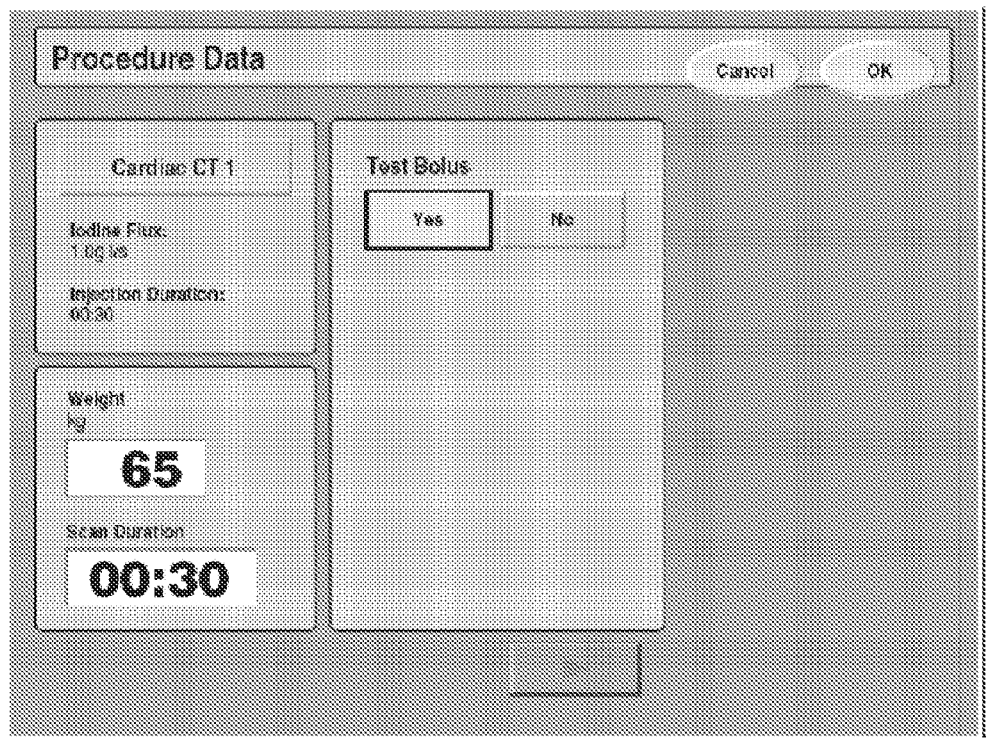
FIG. 19 illustrates an embodiment of a graphical user interface for use with an embodiment of a parameter generator of the present invention.
Figure 20:
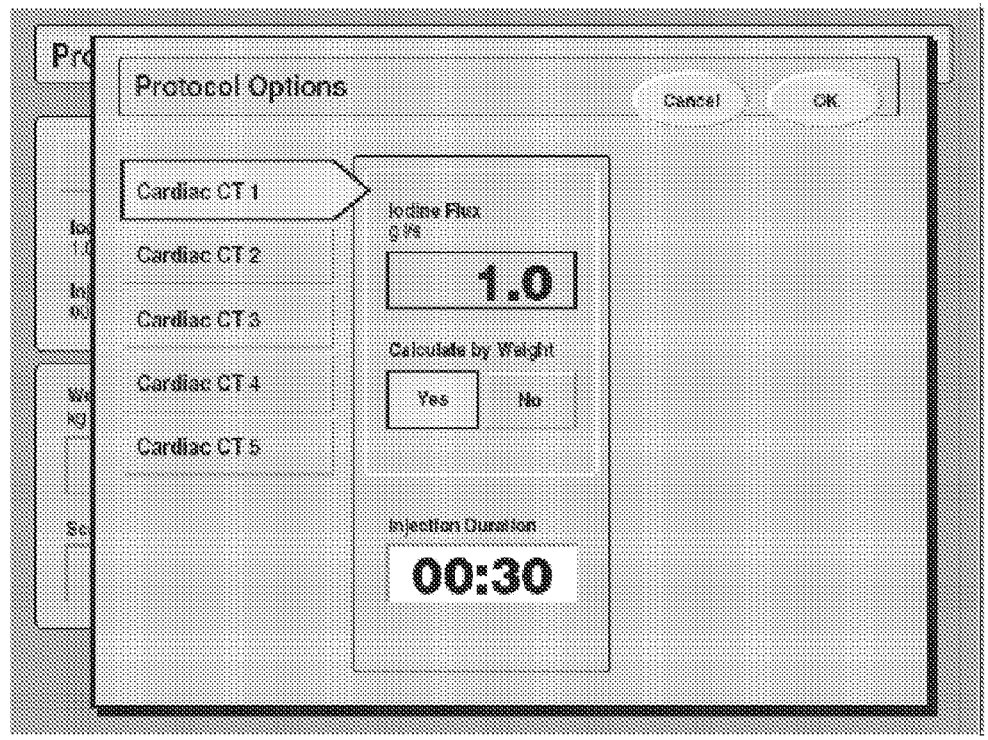
FIG. 20 illustrates another portion of a graphical user interface for use with an embodiment of a parameter generator of the present invention.

FIGS. 19 through 23 illustrate several screen captures of a graphical user interface suitable to effect the dual flow injection protocol determination described above. In FIGS. 19 and 20 the algorithm set forth above in connection with FIGS. 10 through 18 is selected via the designation Cardiac CT1. A patient weight of 65 kg and a test scan duration of 30 seconds are input. An iodine flux of 1.0 g/s is established for the imaging procedure injection. As the concentration of contrast fluid is 250 mgI/ml, a flow rate of 4 ml/s will be used in the imaging procedure injection.

Figure 21:
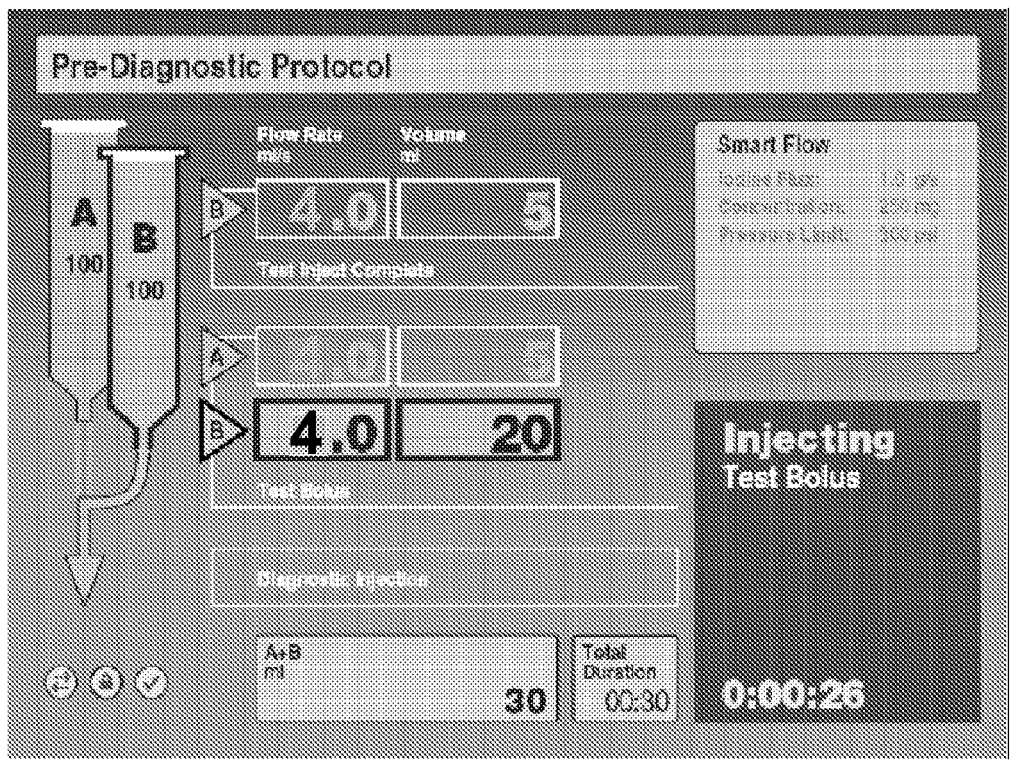
FIG. 21 illustrates another portion of a graphical user interface for use with an embodiment of a parameter generator of the present invention.
Figure 22:
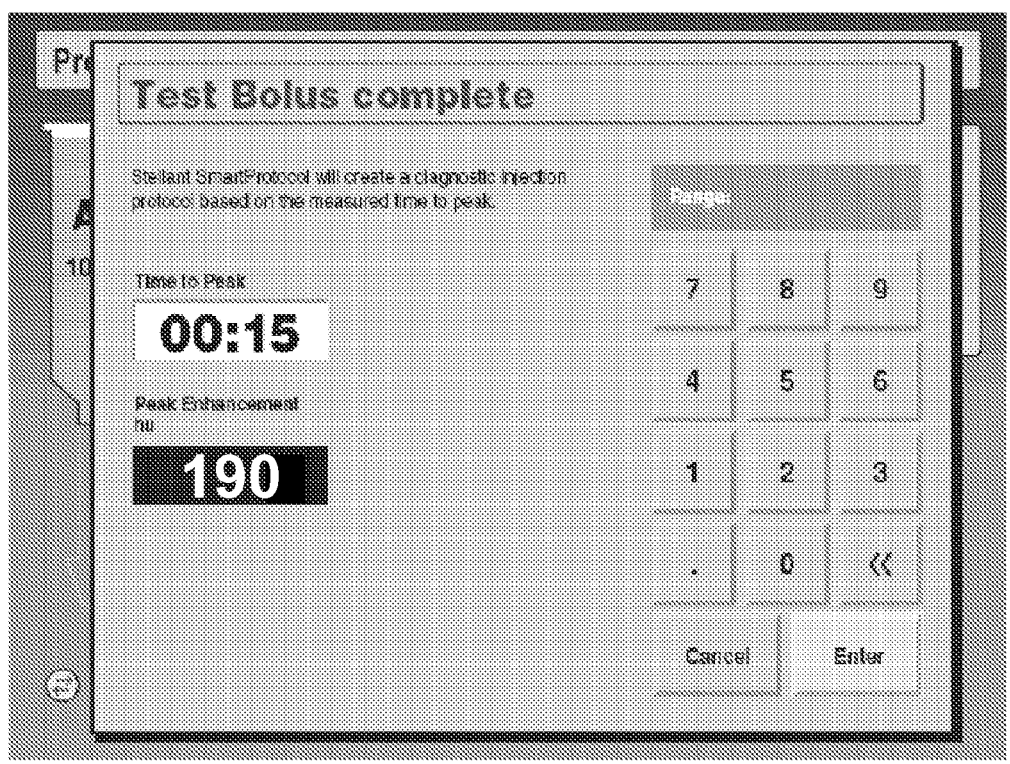
FIG. 22 illustrates another portion of a graphical user interface for use with an embodiment of a parameter generator of the present invention.
Figure 23:
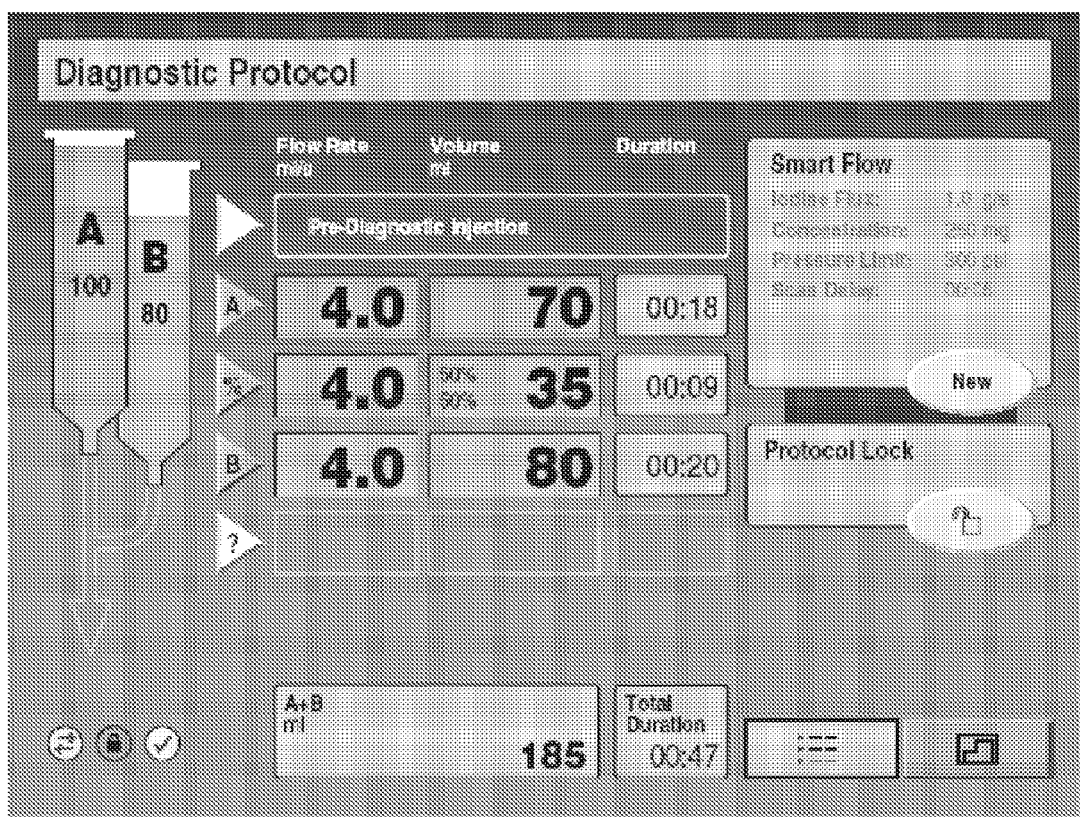
FIG. 23 illustrates another portion of a graphical user interface for use with an embodiment of a parameter generator of the present invention.

As set forth in FIG. 21, the flow rate during the test injection is 1.0 ml/s. During the 30 second test injection a bolus of saline (from source B) is first injected at a flow rate of 4.0 ml/s for 5 seconds. A bolus of contrast (from source A) is then injected at a flow rate of 4.0 ml/s for 5 seconds. Finally, a flushing bolus of saline is injected at a flow rate of 4.0 ml/s for 20 seconds. After the completion of the test bolus injection, the time to peak and the peak enhancement are determined as illustrated in FIG. 22. Using the values set forth above, the diagnostic injection protocol is determined using the system/method described in connection with FIGS. 10 through 18. FIG. 23 sets forth the determined diagnostic injection protocol including the following three phases: (1) injection of a 70 ml volume of contrast (source A) at 4 ml/s (duration of 18 seconds); (2) injection of a 35 ml volume of a 50/50 contrast/saline admixture (dual flow from sources A and B) at 4 ml/s (duration of 9 seconds); and (3) injection of an 80 ml volume of saline (source B) at 4 ml/s (duration 20 seconds). Thus, a total of 185 ml of fluid is injected over a time period (total duration) of 47 seconds. As also set forth in FIG. 23, a pressure limit of 300 psi for the fluid path used in the injection procedure was set. Also, a scan delay of 5 seconds was established.

Figure 24:
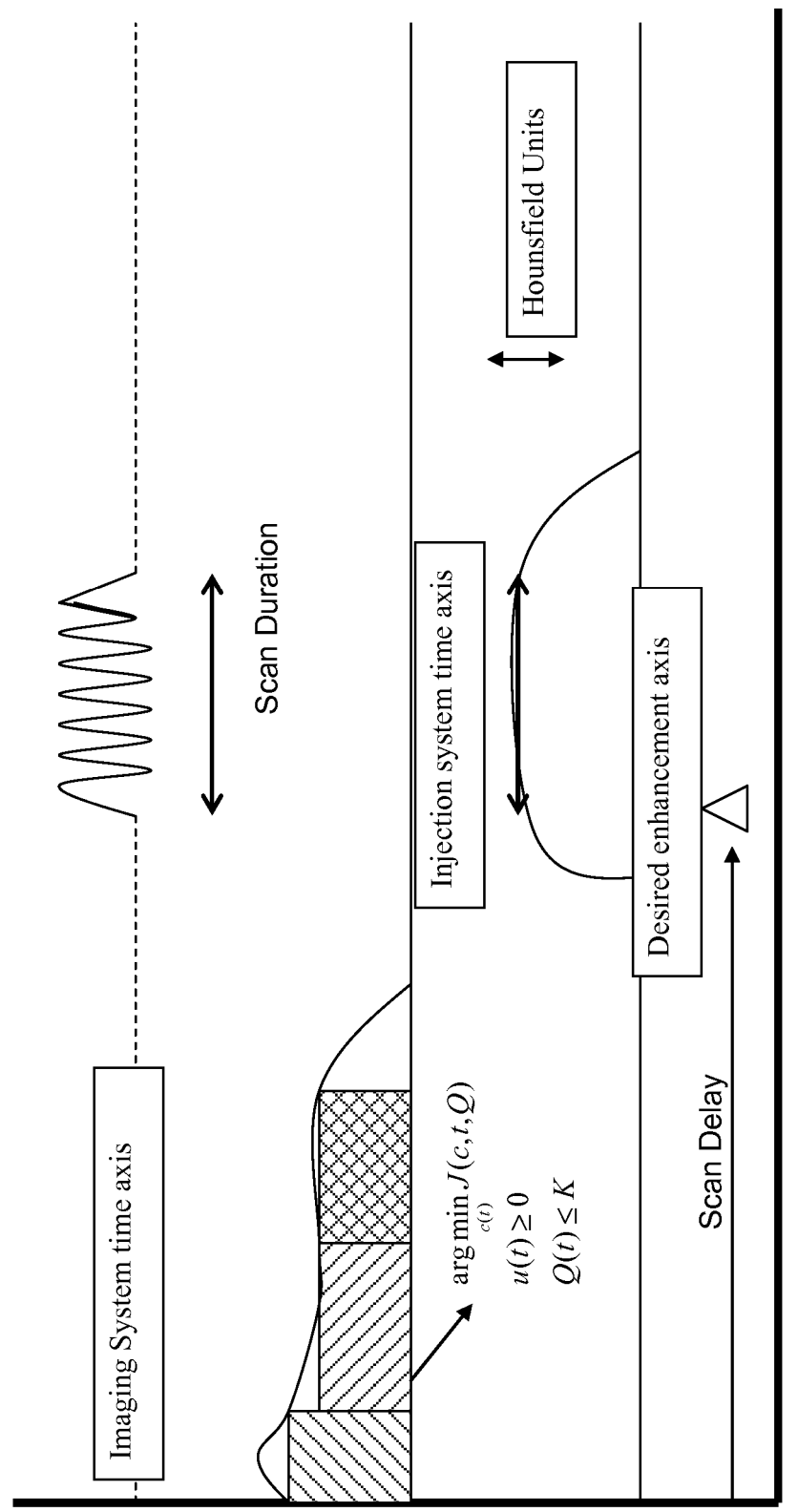
FIG. 24 illustrates a graphical representation of an embodiment of a user interface for interacting with a contrast injection system.

FIG. 24 illustrates a graphical representation of an embodiment of an interface for interacting with a contrast injection system that can, for example, be in operative connection with an imaging system. The bottom axis ("Desired enhancement axis") provides an area for an operator to input (for example, draw) a desired enhancement curve, commencing at a particular time and reaching a certain enhancement value. The operator, for example, can choose multiple imaging sequences and also injections throughout a time interval based on the type of diagnostic procedure to be performed. The top axis presents the timing for an imaging sequence (for example, CT, MRI, PET etc.) in which the duration of the scan sequence is known. Once the operator draws the desired enhancement profile, the injection system computes an injection protocol that will achieve the desired enhancement. Computations necessary to achieve the injection protocol may rely upon a model of the patient, drug and imaging system or can be derived from statistical analysis of explicit feedback from the scanner as, for example, described in PCT International Publication No. WO 2006/055813, the contents of which have been incorporated herein by reference. Once again, using such a model, an operator can enter or draw a contrast injection profile on the "injection system axis", and the resulting enhancement curve from the entered protocol would be presented on the bottom, enhancement axis. The operator can then examine the predicted enhancement and decide if it is satisfactory. If not, the operator can redraw an input function (injection profile/protocol). A computer to iteratively arrive at a predetermined enhancement level can, for example, be used to perform the operation.

The representative embodiments set forth above are discussed primarily in the context of CT imaging. However, the devices, systems and methods of the present invention have wide applicability to the injection of pharmaceuticals. For example, the systems devices and methods of the present invention can be used in connection with the injection of contrast media for imaging procedures other than CT (for example, MRI, ultrasound, PET etc.). In that regard, FIGS. 25A and 25B illustrate one embodiment of the present invention for use with MRI.

Figure 25A:
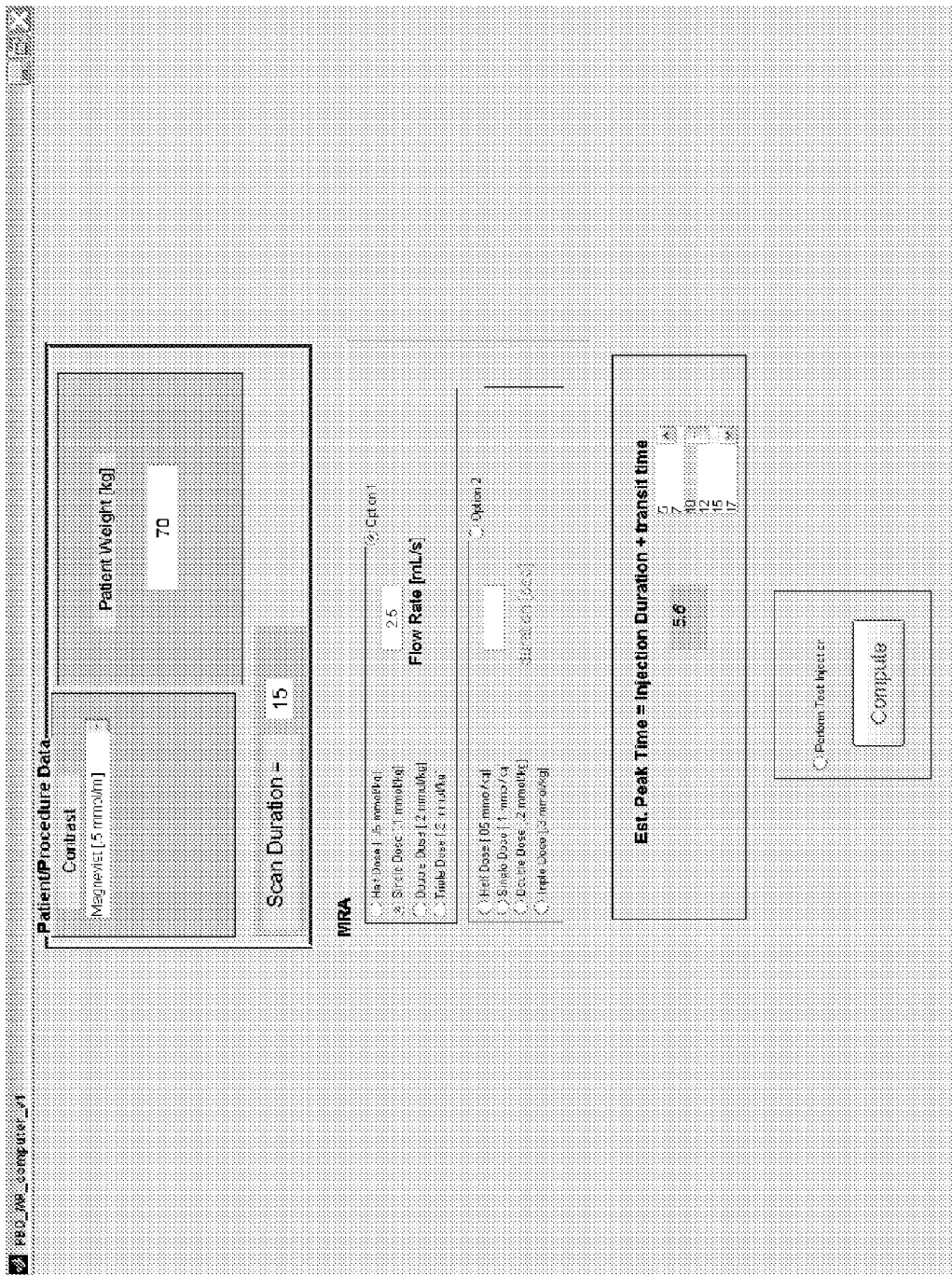
FIG. 25A illustrates a graphical user interface for use with an embodiment of a parameter generator of the present invention for use with MRI.

FIG. 25A illustrates one embodiment of a system to compute an injection profile for an MRI procedure using a Gadolinium agent. The operator chooses the type of drug being injected (for example, from a menu in which the drug/contrast is listed by brand name and/or concentration). The operator then enters the patient's weight and the desired scan duration. Based on the dosing scheme (dose scale) preferred (for example, how many mmol of Gd to deliver per body weight—a standard technique for dosing in MRI procedures), the system computes an appropriate volume and flow rate (if the flow rate is not explicitly entered, as in option 2 of FIG. 25A) as follows:

Volume [ml]=dose scale [mmol/kg]*weight[kg]*(1/concentration [mmol/ml])

The flow rate is computed (in option 2) as follows:

flow rate [ml/s]=Volume [ml]/scan duration [sec]

or flow rate[ml/s]=Volume [ml]/injection duration [sec].

The estimated peak time (of the contrast medium in vivo) is, for example, computed as the duration of the injection plus a constant chosen by the operator. The suggested scan delay is, for example, computed by subtracting one half the scan duration from the estimated time to peak enhancement. FIG. 25B illustrates one embodiment of computed values for a biphasic injection of contrast and saline.

As briefly described above, the flow rate predicted for a phase (or time instance of an injection) can be used as an input to a system or model adapted or operable to predict the amount of pressure generated in the syringe or other container as a result of the volumetric flow rate, the fluid path characteristics (for example, the inner diameter of the catheter (gauge)), and the viscosity of the contrast agent. Generally, the viscosity of contrast medium increases geometrically with respect to the iodine concentration of the contrast medium in the case of a CT contrast. The viscosity can be calculated or retrieved from, for example, a data table. The pressure resulting from a set of values of these variables may be computed from fluid dynamics principles as known in the art or determined from prior experimental data. A PRESSURE MODELING section below sets forth several embodiments of a model or system for predicting pressure at various points in an injection fluid path. If the predicted pressure exceeds a pressure limit or threshold set by the operator and/or a safe pressure limit determined by the manufacturer of the power injector, the operator can be warned of a possible over-pressure indication by, for example, a color coding of the flow rate entry field. Various other visual, audible and/or tactile indications of a predicted over-pressure situation can be provided. One embodiment of a pressure modeling system is set forth generally in FIG. 26.

A number of currently available injectors will inject fluid at a programmed flow rate until the pressure generated in the syringe exceeds a set threshold. When this occurs, the computer controlling the fluid injection reduces the volumetric flow rate until the pressure is not exceeded and the injection continues, albeit at a lower flow rate than initially programmed. Pressure limited operation of an injector is discussed, for example, in U.S. Pat. No. 6,520,930, assigned to the assignee of the present invention, the disclosure of which is incorporated herein by reference. In a number of pressure limiting control schemes, the control computer of the injector endeavors to deliver the programmed volume of fluid by reducing the volumetric flow rate from that programmed to avoid exceeding the pressure limit or threshold. Injection can also be halted if a pressure hazard limit is exceeded.

This mode or operation is not optimal for CT scans performed with, for example, Multi-Detector CT (MDCT). In that regard, a primary factor influencing image enhancement in MDCT procedures is the volumetric flow rate of contrast delivered into the circulatory system. The pressure modeling system of the present invention addresses this problem by alerting the operator before the injection commences that the choice of injection parameters will result in an over-pressure situation. The operator can thus alter the injection parameters to avoid the over-pressure situation and the associated variation from the programmed volumetric flow rate.

After resolving any potential over-pressure situations, the system can insert numerical values in the remaining phases of the protocol. The last phase can, for example, be a saline phase (from the $2^{nd}$ or B fluid path) at a volume of, for example, 40 ml at the flow rate of the preceding phase.

The operator can be given the choice to override any or all of the parameters presented in the protocol interface. If the values are acceptable to the operator, then the system is armed and the injection continues.

If a test injection is chosen, the system performs the test injection of contrast medium followed by an injection of saline and then a hold or pause. The operator may then enter a scanning delay. The present invention can provide the operator with a set of options to choose a scan delay (the time from the commencement of the contrast injection to when the diagnostic scan should begin). As depicted, for example, in FIGS. 4 through 6, the operator may choose from an option of several delays. Moreover, a scan delay can be automatically generated from, for example, an analysis of a test injection.

Pressure Modeling

To adequately and efficiently control injector pressure in an injector system, it is desirable to be able to predict the pressure at various points in the flow path of the injector system during an injection. To predict such pressures, one can mathematically model the flow through the injector flow path using equations of state.

Figure 26:
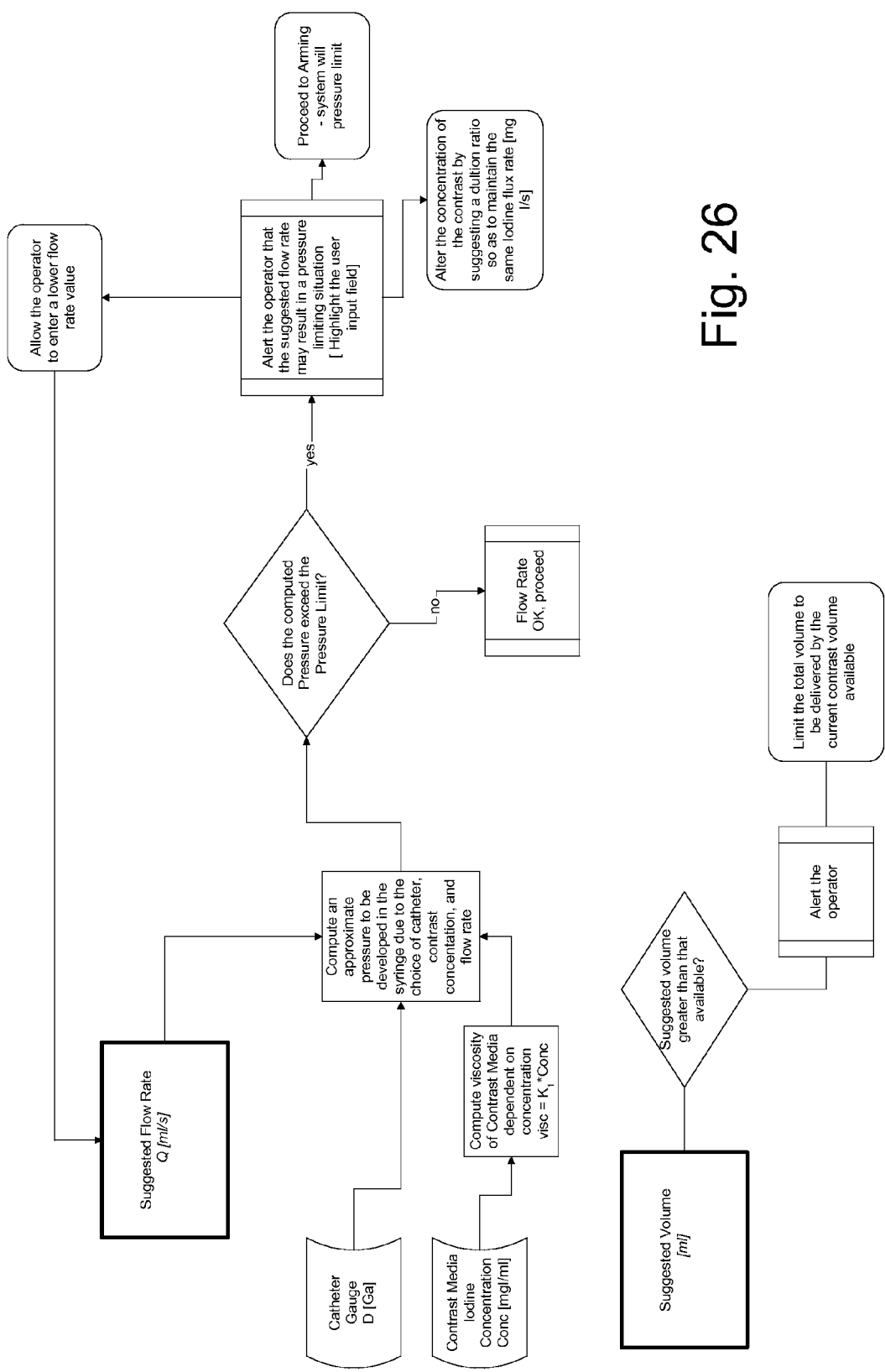
FIG. 26 illustrates an embodiment of a pressure modeling or pressure prediction system of the present invention.

In one embodiment of a mathematical or numerical model for calculating pressure at various points in an injector system flow path of the present invention, the following assumptions were made: the flow is steady; the flow is uniform; a Newtownian fluid is present in the system; the continuity equation is valid throughout the flow geometry (that is, the mass flux of liquid exiting the tip of the syringe is the same as that exiting the catheter—$Q_{in}=Q_{out}$ in FIG. 26); and the pressure within the entire syringe is the same as at the tip of the syringe.

By assuming that the spatial domain of interest is enclosed within a fixed control volume (inertial reference frame), the general energy equation can be used to describe the behavior of fluids throughout the volume. See, for example, Potter and Swiggert, *Fluid Mechanics*. Englewood Hills, N.J.: Prentice Hill, 1992, the disclosure of which is incorporated herein by reference. Using vector notation, the most general form of the energy equation for steady fluid flow through a stationary, closed control volume is:

$$\sum \frac{W}{mg} = \oint_{c.v.} \left( \frac{\bar{V}^2}{2} + \frac{p}{\rho} + gz \right) \rho \bar{V} \cdot \hat{n} dA + losses \quad \text{Equation 1}$$

with the constraint (continuity equation) for steady flow through stationary control volume:

$$0 = \oint_{c.v.} \rho \bar{V} \cdot \hat{n} dA \quad \text{Equation 2}$$

The "losses" term in Equation 1 represents losses arising from thermal exchange, boundary layer interaction, wall shear, viscous heating, and geometry losses (resulting from tubing constriction, valves, coiling, etc.). If one imposes the condition that flow throughout the spatial domain is uniform (the flow rate (dV/dt) is constant throughout), Equation 1 can be simplified to the familiar Bernoulli equation (with the addition of the "loss" terms specified before—$H_{LOSS}$). See, for example, Baker A, Sanders J., "Fluid Mechanics Analysis of a Spring-Loaded Jet Injector", *IEEE Transactions on Biomedical Engineering*, vol. 46, No 2., February 1999, the disclosure of which is incorporated herein by reference.

$$\frac{p_{out}}{\gamma} + H_{Loss} + \frac{\bar{V}_{out}^2}{2g} = \frac{p_{in}}{\gamma} + \frac{\bar{V}_{in}^2}{2g} \quad \text{Equation 3}$$

In Equation 3, $\gamma=\rho g$ (specific mass of the fluid), wherein $\rho$ is the density of the fluid and g is gravitational acceleration. Equations 1 through 3 are expressed in dimensional units of length. To express the result in pressure units, one must multiply both sides by the specific mass of the fluid $\gamma$. $H_{Loss}$ in Equation 3 is the sum of the geometry losses and the losses resulting from the viscous properties of the fluid as set forth in Equation 4:

$$H_{Loss} = \left( \sum_{i=1}^{N} K_i \frac{\bar{V}^2}{2g} \right) + f \frac{L_{LLPCT}}{D_{LLPCT}} \frac{\bar{V}^2}{2g} + f \frac{L_{cath}}{D_{cath}} \frac{\bar{V}^2}{2g} \quad \text{Equation 4}$$

The velocities presented in Equations 1 through 3 are averaged quantities. Because we are primarily interested in volume per unit time, average linear velocities (the velocity of a cell of liquid along a streamline) may be changed to flow rates by the following relation:

$$\bar{V} = \frac{\int \bar{V} dA}{A} = \frac{Q}{A} \quad \text{Equation 5}$$

It is common in many engineering calculations to ignore the kinetic energy component of Equation 1 (the $V^2/2$ term) when the average fluid velocities are low. However, because of the small opening of intravenous catheters through which the injection fluid (for example, contrast agent) must exit, the linear velocity components of the fluid may become non-trivial, thus contributing to the overall pressure head developed in the syringe.

The first term in Equation 4 is the loss factor for the "minor" losses in the system. The K terms in Equation 4 are numerical values determined by empirical analysis and found in most fluid dynamics text books. See, for example, Potter and Swiggert, *Fluid Mechanics*. Englewood Hills, N.J.: Prentice Hill, 1992. The three terms considered in the model of the present invention are:

$K_{valve}$—losses attributable to a "stop-cock" in line with the fluid path. When the valve is open, this coefficient goes to 0.

$K_{coil}$—loss attributable to the coiled effect of the low pressure connector (LPCT) tubing. The model and subsequent simulation uses a value of 80, which was determined by multiplying the loss coefficient for a single 90 degree bend ($K\approx 0.45$) by 4 (for one loop of the LPCT) and then again by 30 (roughly the number of loops in a 96" LPCT). This operation results in a product of 54. A value of 26 was added to the product after comparing simulation outputs with experimental data. Simulation resulting from use of a coil loss of 80 fit the experimental data fairly well. However, it is possible to further optimize this coefficient with respect to experimental data sets.

$K_{contraction}$—loss attributable to the pressure generated when the fluid is forced from the larger diameter LPCT into the smaller diameter catheter. The value of this coefficient may again be found in fluid textbooks. The actual value of the constant is dependent on the ratio of the LPCT's area to the catheter's area. The following relationship exists between the two areas and the coefficient (as presented by Potter and Swiggert):

TABLE 1

| Area Ratio | Value Of $K_{contraction}$ |
|---|---|
| 2:1 | .25 |
| 5:1 | .41 |
| 10:1 | .46 |

The relationship in Table 1 may be interpolated for values not directly specified.

The second and third terms in Equation 4 describe the energy lost (or pressure needed to maintain flow) in the fluid path resulting from the viscous properties of the contrast media. For laminar, viscous flow in a tube, the f term correlating to a friction factor can be expressed as:

$$f = \frac{64}{\text{Re}} \quad \text{Equation 6}$$

The Reynolds Number Re is a ratio of the inertial forces to internal viscous forces for an infinitesimal volume of fluid along a streamline. With relation to flow rate (Q), the Reynolds Number can be expressed as:

$$\text{Re} = \frac{4Q\rho}{\pi D \mu} \quad \text{Equation 7}$$

where $\rho$ is, once again, the fluid's density, D is the tube's diameter, and $\mu$ is the fluid's viscosity. As evidenced by Equation 7, if the fluid's viscosity increases Re will decrease (for a fixed D and $\rho$). If the tube's diameter decreases, the Reynolds Number will also increase (for a fixed $\rho$ and $\mu$). Substituting Equation 6 and Equation 7 into Equation 4, one derives a function for pressure dependent on flow rate, viscosity, length and diameter when the flow is laminar:

$$\Delta p = \frac{128 Q \mu L}{\pi D^4} \quad \text{Equation 8}$$

wherein $\Delta p = p_{syr} - p_{exit}$, assuming that $p_{exit} = p_{gauge} = p_0 = 0$.

In addition to the assumptions set forth above, neglecting the impact of gravity, and including the "minor" losses (resulting from geometry and coiling) and losses resulting from fluid viscosity, Equation 1 can be restated and solved for the pressure at the tip of the syringe (laminar flow—Re less than 2500) as follows:

$$\Delta p_{syr} = \frac{8\rho Q^2}{\pi^2 D^4} \sum_{i=1}^{3} K_i + \frac{128 Q \mu L_{LLPCT}}{\pi D_{LLPCT}^4} + \frac{128 Q \mu L_{cath}}{\pi D_{cath}^4} + \frac{\rho}{2} Q^2 \left( \frac{1}{A_{cath}^2} - \frac{1}{A_{LLPCT}^2} \right) \quad \text{Equation 9}$$

Because of fluid viscosity, complex interactions occur among boundary layers in pipes/tubes. When flow exceeds a critical threshold, the boundary layers may begin to interact (termed boundary layer shedding), and the flow may become turbulent. When flow is turbulent (or near turbulent), the standard assumption of Poiseuille flow (a parabolic flow profile) is not sufficient to predict pressure vs. flow dependencies. The friction term in Equation 6 is applicable only when the flow is in the laminar region.

To fully describe turbulent flow, one must solve a time averaged Navier-Stokes along the boundary of interest. This solution is extremely difficult as the Navier-Stokes equations are highly non-linear and extremely sensitive to initial condition perturbations. Several empirical methods have been developed to approximate the fluid performance in a turbulent regime. Moody published a series of curves correlating the friction factor to Reynolds Number. Theses charts are based on experiments performed in the late 1940s. Colebrook fit equations to these curves and derived an analytic expression relating the friction factor to the Reynolds Number, pipe diameter, and wall roughness. Swamee and Jain developed a more exact relationship between a tube's physical parameters and the pressure head generated across it. They developed an empirically derived equation for flow turbulence, and this relationship is used in one embodiment of the fluid model of the present invention. In the Swammee-Jain approximation for turbulent flow, the pressure drop across a length of tubing L, having diameter D, and wall roughness e is expressed by:

$$\Delta p = \frac{1.07 Q^2 L \rho}{D^5} \frac{1}{\left[ \ln\left[ \frac{e}{3.7D} + 4.62\left(\frac{\mu D}{\rho Q}\right)^{.9} \right] \right]^2} \quad \text{Equation 10}$$

Figure 27:
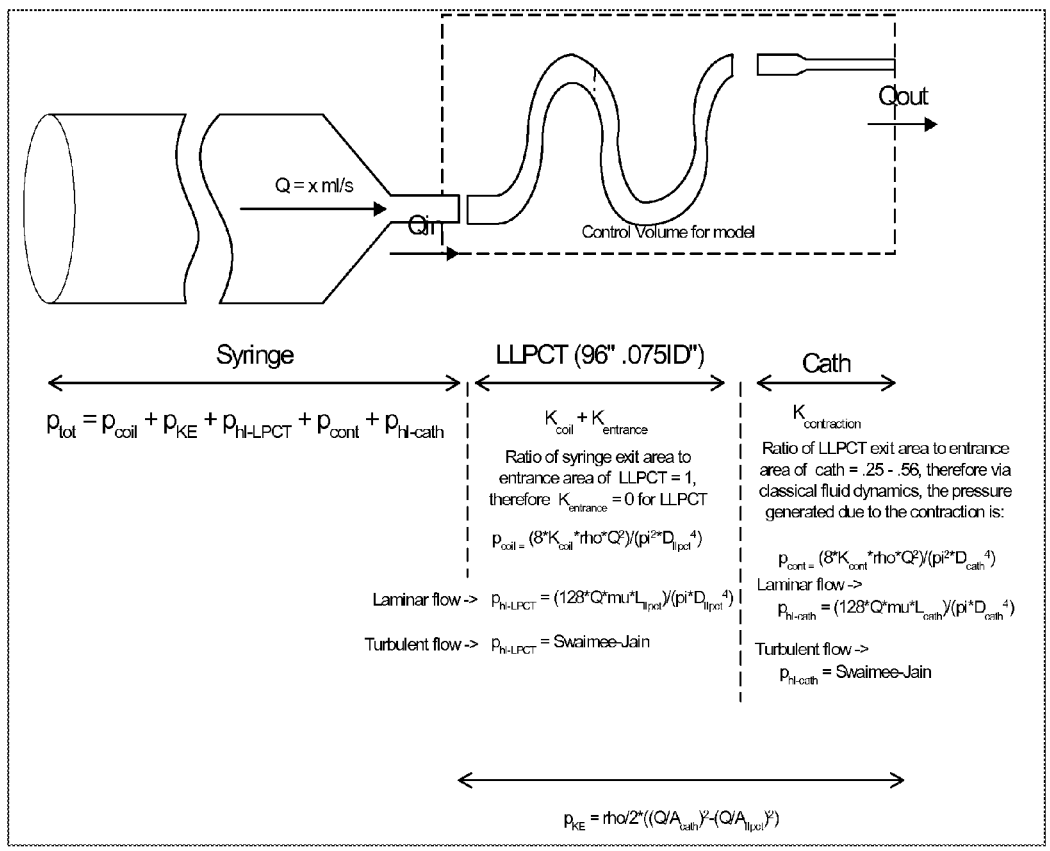
FIG. 27 illustrates pressure modeling in several section of a fluid path.

The value of the Reynolds Number dictates whether the model of the present invention uses Equation 8 or Equation 10 to predict pressures. There is never a clean transition from laminar flow into turbulent flow. In engineering fluid modelling, typically flows having Reynolds Numbers greater than 2500 are considered turbulent (thus Equation 10 is applicable), although the true change to turbulent flow can happen at much greater Reynolds numbers dependent on the stability of the flow and other properties of the flow field. A region known as the transition zone lies between laminar flow and turbulent flow. It is very difficult to accurately describe the fluid dynamics in the transition zone, especially for fast flow through narrow tubes, which can account for some of the error observed when comparing theoretical descriptions of injector fluid paths to empirical results. The model used in the present invention transitioned from laminar flow to turbulent flow (that is, transitioned from Equation 8 to Equation 10) when the Reynolds Number exceeds 2500. The above discussion above is summarized schematically in FIG. 27.

With the addition of the turbulent flow description, the model predicts the pressure across the fluid path as:

$$\Delta p_{syr} = \frac{8\rho Q^2}{\pi^2 D^4} \sum_{i=1}^{3} K_i + \frac{1.07 Q^2 L_{LLPCT} \rho}{D_{LLPCT}^5} \frac{1}{\left[ \ln\left[ \frac{e}{3.7 D_{LLPCT}} + 4.62\left(\frac{\mu D_{LLPCT}}{\rho Q}\right)^{.9} \right] \right]^2} + \frac{\rho}{2} Q^2 \left( \frac{1}{A_{cath}^2} - \frac{1}{A_{LLPCT}^2} \right) + \frac{1.07 Q^2 L_{cath} \rho}{D_{cath}^5} \frac{1}{\left[ \ln\left[ \frac{e}{3.7 D_{cath}} + 4.62\left(\frac{\mu D_{cath}}{\rho Q}\right)^{.9} \right] \right]^2}$$

Equation 11 Pressure generation equation for fluid model assuming turbulent flow (Reynolds No.>2500, $e=1\times10^{-5}$ for plastic tubing).

Figure 28:
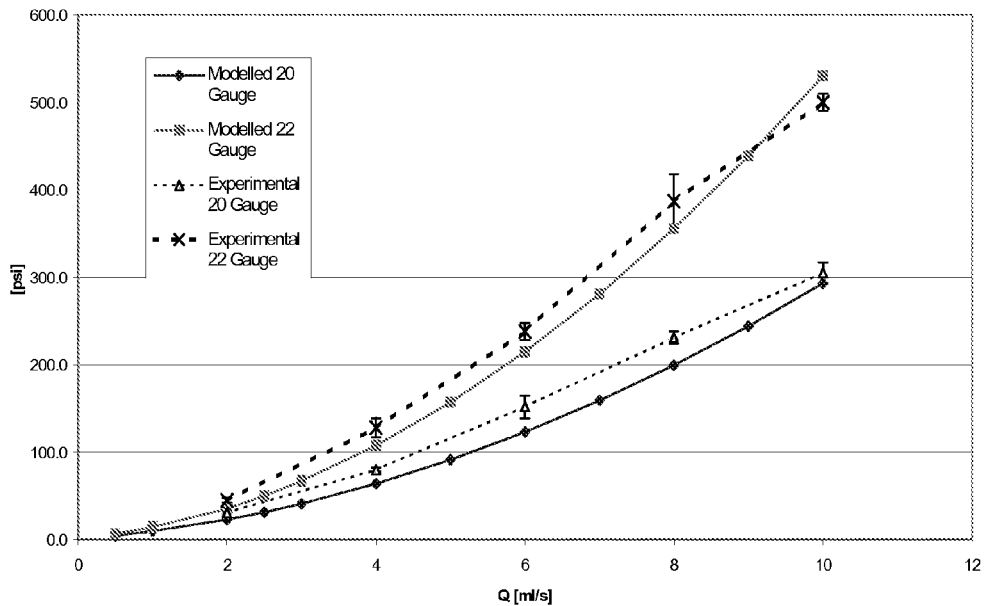
FIG. 28 illustrates graphically a pressure prediction curve determined by an embodiment of a pressure model of the present invention for flow of MAGNEVIST contrast through the system.
Figure 29:
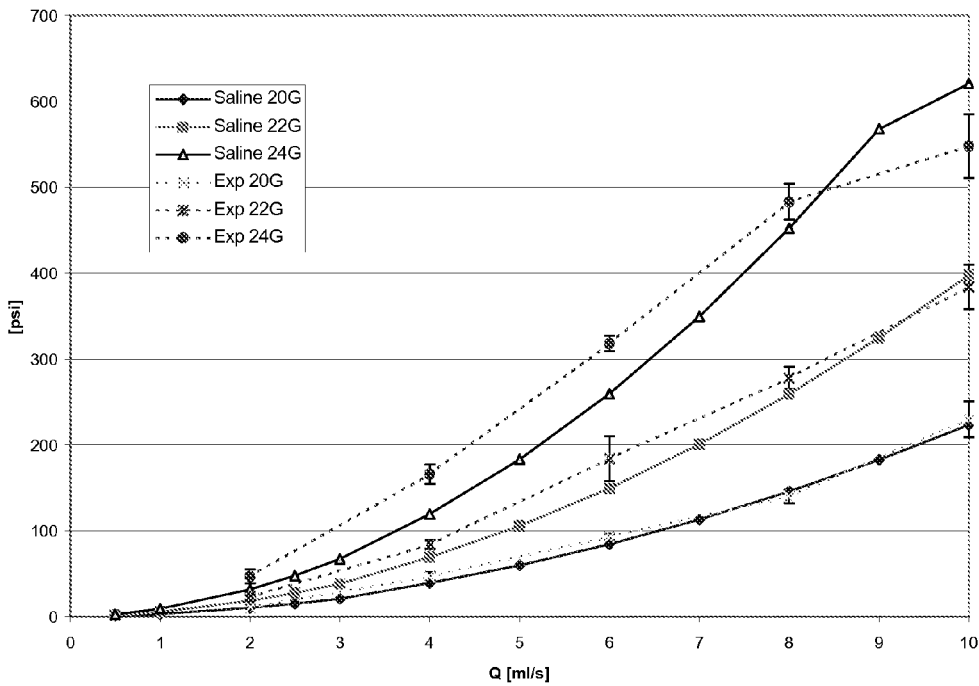
FIG. 29 illustrates graphically a pressure prediction curve determined by an embodiment of a pressure model of the present invention for flow of saline through the system.
Figure 30:
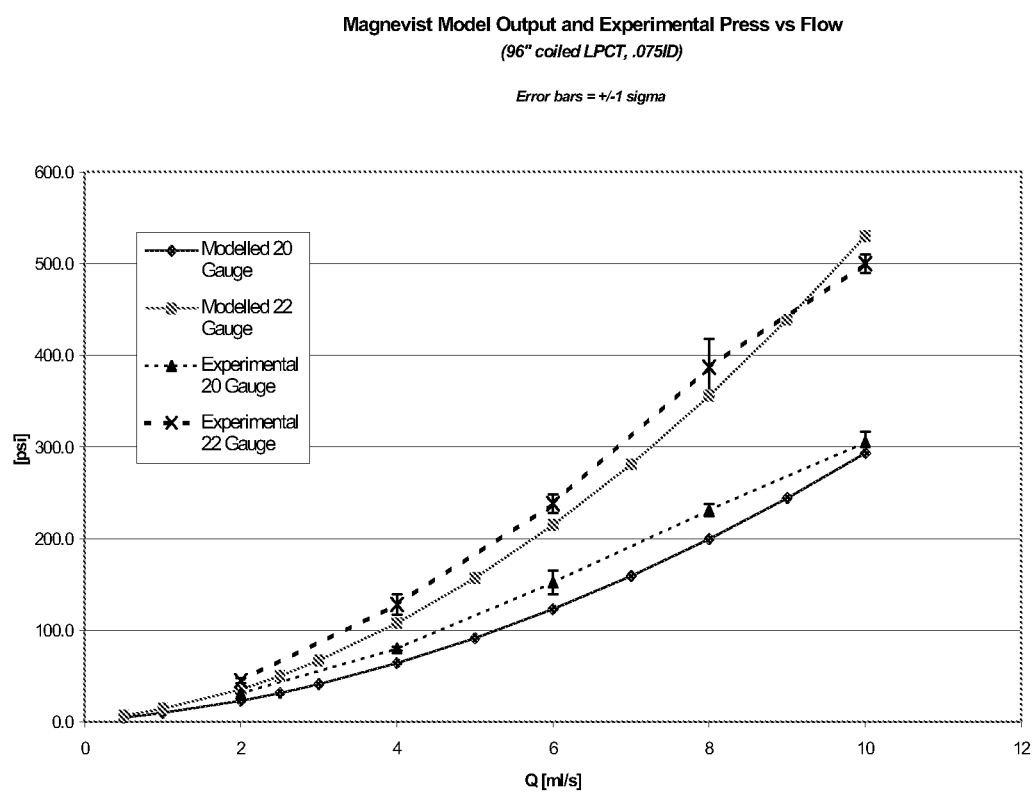
FIG. 30 illustrates graphically a pressure prediction curve determined by an embodiment of a pressure model of the present invention for flow of MAGNEVIST contrast through the system.

FIGS. 28 through 30 illustrate graphs of pressured predicted by the analytical model described above. The experimental data are taken from a study testing the pressure performance of MR disposable components (0.075" ID LLPCT, 20-24 ga Angiocath catheters) with various MR contrast agents (Gadovist, Magnevist, and Saline were tested). The pressure data generated from the model are outputs of the model assuming the flow has achieved steady state. As one can see in the figures, there is good agreement between the theoretical predictions and the experimentally determined pressures. The error bars about each experimental point are +/−1 standard deviation of the sample taken for each flow rate. There were 5 pressure samples taken at each flow rate in that study. The above computations can be made more precise if measurements of pressure were available to the system via sensors located within the fluid path, for example MEMS transducers manufactured by Verimetra Inc. of Pittsburgh Pa.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A fluid injection apparatus comprising:
   (a) at least one pressurizing mechanism to which a fluid path is operably connectible, the fluid path comprising at least one fluid container for containing at least one fluid therein, tubing operatively connectible to an outlet of the at least one fluid container, and a catheter operatively connectible to the tubing, the at least one pressurizing mechanism for pressurizing the at least one fluid within the at least one fluid container so as to inject the at least one fluid therein into the patient via the tubing and the catheter; and
   (b) a controller operably associated with the at least one pressurizing mechanism and comprising a programming system, the programming system (I) enabling input by an operator thereof of a desired injection protocol of an injection procedure according to which the at least one fluid is intended to be injected into the patient and (II) having at least one algorithm for predicting an expected pressure level that would result at at least one point in the fluid path if the desired injection protocol were to be carried out by the fluid injection apparatus, the expected pressure level being determined before commencement of the desired injection protocol according to a pressure model in which at least one of a plurality of parameters relevant to the injection procedure is used as an input, the at least one of the plurality of parameters being selected from the group consisting of an inner diameter of the catheter and a hydraulic resistance of the catheter, the at least one algorithm being adapted to determine the expected pressure level before commencement of the desired injection protocol for a plurality of catheters of differing diameters; the at least one algorithm further (A) if the expected pressure level is less than or equal to a pressure threshold value, enabling the desired injection protocol to be carried out by the fluid injection apparatus and (B) if the expected pressure level exceeds the pressure threshold value, alerting the operator whereupon the operator is enabled to choose between one of (i) permitting the desired injection protocol to be carried out by the fluid injection apparatus as programmed and (ii) changing at least one of the plurality of parameters and thereby update the desired injection protocol so that once the expected pressure level is determined via the pressure model to be less than or equal to the pressure threshold value, the desired injection protocol is enabled to be carried out by the fluid injection apparatus.

2. The fluid injection apparatus of claim 1, wherein the pressure threshold value is set by one of (i) the operator of the fluid injection apparatus and (ii) a manufacturer of the fluid injection apparatus.

3. The fluid injection apparatus of claim 1, wherein the at least one of the plurality of parameters of the injection procedure used in determining the expected pressure level according to the pressure model also includes a volumetric flow rate of the at least one fluid, a viscosity of the at least one fluid, and at least one characteristic of the tubing.

4. The fluid injection apparatus of claim 3, wherein the at least one characteristic of the tubing includes at least one of (i) an inner diameter of the tubing, (ii) a compliance of the tubing, and (iii) a hydraulic resistance of the tubing.

5. The fluid injection apparatus of claim 1, wherein when the expected pressure level is determined via the pressure model to be in excess of the pressure threshold value, the at least one of the plurality of parameters that the operator may change to update the desired injection protocol includes at least one of (i) a flow rate of the at least one fluid, (ii) a concentration of the at least one fluid, and (iii) a ratio of one fluid of the at least one fluid to another fluid of the at least one fluid.

6. A method of predicting pressure at at least one point within a fluid path comprising tubing and a catheter operatively connectible to the tubing and into which at least one fluid is introduced, the method comprising:
   (a) planning a desired injection protocol according to which the at least one fluid is intended to be introduced into the fluid path under pressure via at least one pressurizing mechanism for pressurizing the at least one fluid;
   (b) predicting an expected pressure level that would result at at least one point in the fluid path if the desired injection protocol were to be used as intended to introduce the at least one fluid into the fluid path, the expected pressure level being determined before commencement of the desired injection protocol according to a pressure model in which at least one of a plurality of parameters relevant to the desired injection protocol is used as an input, the at least one of the plurality of parameters being selected from the group consisting of an inner diameter of the catheter and a hydraulic resistance of the catheter;
   (c) if the expected pressure level is less than or equal to a pressure threshold value, enabling the desired injection protocol to be used as intended to introduce the at least one fluid into the fluid path; and
   (d) if the expected pressure level exceeds the pressure threshold value, performing one of:
      (I) alerting a user of the method thereof whereupon the user is enabled to choose between one of (i) permitting the desired injection protocol to be used as intended to introduce the at least one fluid into the fluid path and (ii) changing at least one of the plurality of parameters and thereby update the desired injection protocol so that once the expected pressure level is determined via the pressure model to be less than or equal to the pressure threshold value, the desired injection protocol is enabled to be used to introduce the at least one fluid into the fluid path; and
      (II) automatically changing at least one of the plurality of parameters and thereby update the desired injection protocol so that the expected pressure level will be determined via the pressure model to be less than or equal to the pressure threshold value thereby enabling the desired injection protocol to be used to introduce the at least one fluid into the fluid path.

7. The method of claim 6, wherein the at least one fluid is introduced into the fluid path by a fluid injection apparatus operating according to the desired injection protocol, the fluid injection apparatus having the at least one pressurizing mechanism for pressurizing the at least one fluid and a controller operably associated therewith through which to program the desired injection protocol according to which the at least one fluid is intended to be introduced into the fluid path and therethrough injected into a patient.

8. The method of claim 7, wherein the pressure threshold value is set by one of (i) an operator of the fluid injection apparatus and (ii) a manufacturer of the fluid injection apparatus.

9. The method of claim 6, wherein the at least one of the plurality of parameters of the desired injection protocol used in determining the expected pressure level according to the pressure model includes a volumetric flow rate of the at least one fluid, a viscosity of the at least one fluid, and at least one characteristic of the tubing.

10. The method of claim 9, wherein the at least one characteristic of the tubing includes at least one of (i) an inner diameter of the tubing, (ii) a compliance of the tubing and (iii) a hydraulic resistance of the tubing.

11. The method of claim 6, wherein when the expected pressure level is determined via the pressure model to be in excess of the pressure threshold value the at least one of the plurality of parameters that the user may change to update the desired injection protocol includes at least one of (i) a flow rate of the at least one fluid, (ii) a concentration of the at least one fluid, and (iii) a ratio of one fluid of the at least one fluid to another fluid of the at least one fluid.

12. An apparatus for predicting pressure at at least one point within a fluid path comprising tubing and a catheter connectible to the tubing into which at least one fluid is introduced for injection into a patient, the apparatus comprising:
(a) a controller for controlling at least one pressurizing mechanism through which the at least one fluid from at least one fluid container therefor is pressurized through the fluid path for injection into the patient; and
(b) a programming system operably associated with the controller, the programming system (I) enabling input by an operator thereof of a desired injection procedure according to which the at least one fluid is intended to be injected into the patient and (II) having at least one algorithm for predicting an expected pressure level that would result at the at least one point in the fluid path if the desired injection procedure were to be carried out by the apparatus, the expected pressure level being determined before commencement of the desired injection procedure according to a pressure model using at least one of a plurality of parameters on which the desired injection procedure is based, the at least one of the plurality of parameters being selected from the group consisting of an inner diameter of the catheter and a hydraulic resistance of the catheter; the at least one algorithm further (A) if the expected pressure level is less than or equal to a pressure threshold value, enabling the desired injection procedure to be carried out by the apparatus and (B) if the expected pressure level exceeds the pressure threshold value, alerting the operator whereupon the operator is enabled to choose between one of (i) permitting the desired injection procedure to be carried out by the apparatus as programmed and (ii) changing at least one of the plurality of parameters and thereby update the desired injection procedure so that once the expected pressure level is determined via the pressure model to be less than or equal to the pressure threshold value the desired injection procedure is enabled to be carried out by the apparatus.

13. The apparatus of claim 12, wherein the pressure threshold value is set by one of (i) the operator of the apparatus and (ii) a manufacturer of the apparatus.

14. The apparatus of claim 12, wherein the at least one of the plurality of parameters of the injection procedure used in determining the expected pressure level according to the pressure model includes a volumetric flow rate of the at least one fluid, a viscosity of the at least one fluid, and at least one characteristic of the tubing.

15. The apparatus of claim 14, wherein the at least one characteristic of the tubing includes at least one of (i) an inner diameter of the tubing, (ii) a compliance of the tubing and (iii) a hydraulic resistance of the tubing.

16. The apparatus of claim 12, wherein when the expected pressure level is determined via the pressure model to be in excess of the pressure threshold value the at least one of the plurality of parameters that the operator may change to update the desired injection procedure includes at least one of (i) a flow rate of the at least one fluid, (ii) a concentration of the at least one fluid, and (iii) a ratio of one fluid of the at least one fluid to another fluid of the at least one fluid.

17. An apparatus for predicting pressure at at least one point within a fluid path comprising tubing and a catheter connectible to the tubing into which at least one fluid is introduced for injection into a patient, the apparatus comprising:
(a) a controller for controlling at least one pressurizing mechanism through which the at least one fluid from at least one fluid container therefor is pressurized through the fluid path into the patient; and
(b) a programming system operably associated with the controller, the programming system (I) enabling input by an operator thereof of a desired injection procedure according to which the at least one fluid is intended to be injected into the patient and (II) having at least one algorithm for predicting an expected pressure level that would result at the at least one point in the fluid path if the desired injection procedure were to be carried out by the apparatus, the expected pressure level being determined before commencement of the desired injection procedure according to a pressure model in which at least one of a plurality of parameters relevant to the injection procedure is used as an input, the at least one of the plurality of parameters being selected from the group consisting of an inner diameter of the catheter and a hydraulic resistance of the catheter; the at least one algorithm further (A) if the expected pressure level is less than or equal to a pressure threshold value, enabling the desired injection procedure to be carried out by the apparatus and (B) if the expected pressure level exceeds the pressure threshold value, enabling the controller to automatically change at least one of the plurality of parameters and thereby update the desired injection procedure so that once the expected pressure level is determined via the pressure model to be less than or equal to the pressure threshold value the desired injection procedure is enabled to be carried out by the apparatus.

18. The apparatus of claim 17, wherein the pressure threshold value is set by one of (i) the operator of the apparatus and (ii) a manufacturer of the apparatus.

19. The apparatus of claim 17, wherein the at least one of the plurality of parameters of the injection procedure used in determining the expected pressure level according to the pressure model includes a volumetric flow rate of the at least one fluid, a viscosity of the at least one fluid, and at least one characteristic of the tubing.

20. The apparatus of claim 19, wherein the at least one characteristic of the tubing includes at least one of (i) an inner diameter of the tubing, (ii) a compliance of the tubing and (iii) a hydraulic resistance of the tubing.

21. The apparatus of claim 17, wherein when the expected pressure level is determined via the pressure model to be in excess of the pressure threshold value the at least one of the plurality of parameters that the operator may change to update the desired injection procedure includes at least one of (i) a flow rate of the at least one fluid, (ii) a concentration of the at least one fluid, and (iii) a ratio of one fluid of the at least one fluid to another fluid of the at least one fluid.

\* \* \* \* \*